(12) United States Patent
Kuriyama

(10) Patent No.: US 9,462,192 B2
(45) Date of Patent: Oct. 4, 2016

(54) AUTOMATIC EXPOSURE CONTROL DEVICE, CONTROL DEVICE, ENDOSCOPE DEVICE AND AUTOMATIC EXPOSURE CONTROL METHOD

(71) Applicant: OLYMPUS CORPORATION, Shibuya-ku, Tokyo (JP)

(72) Inventor: Naoya Kuriyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 500 days.

(21) Appl. No.: 14/098,316

(22) Filed: Dec. 5, 2013

(65) Prior Publication Data

US 2014/0092226 A1 Apr. 3, 2014

Related U.S. Application Data

(63) Continuation of application No. PCT/JP2012/063594, filed on May 28, 2012.

(30) Foreign Application Priority Data

Aug. 25, 2011 (JP) .................................. 2011-183593

(51) Int. Cl.
| | |
|---|---|
| H04N 5/235 | (2006.01) |
| A61B 1/06 | (2006.01) |
| H04N 5/217 | (2011.01) |
| A61B 1/00 | (2006.01) |
| G02B 23/24 | (2006.01) |

(52) U.S. Cl.
CPC ......... *H04N 5/2353* (2013.01); *A61B 1/00009* (2013.01); *A61B 1/00096* (2013.01); *A61B 1/00163* (2013.01); *A61B 1/00181* (2013.01);

(Continued)

(58) Field of Classification Search
CPC . G02B 23/2469; H04N 5/217; H04N 5/2353
See application file for complete search history.

(56) References Cited

U.S. PATENT DOCUMENTS

| | | | | |
|---|---|---|---|---|
| 4,845,554 A | * | 7/1989 | Kimura | ............... H04N 5/2354 348/216.1 |
| 2011/0273784 A1 | | 11/2011 | Mizusawa | |

(Continued)

FOREIGN PATENT DOCUMENTS

| | | |
|---|---|---|
| EP | 2716206 A1 | 4/2014 |
| JP | 05-130973 A | 5/1993 |

(Continued)

OTHER PUBLICATIONS

Extended European Search Report dated Mar. 17, 2015, issued in counterpart European Application No. 12825059.4.

(Continued)

*Primary Examiner* — Andy Rao
*Assistant Examiner* — Tyler Edwards
(74) *Attorney, Agent, or Firm* — Holtz, Holtz & Volek PC

(57) ABSTRACT

An automatic exposure control device includes an image acquisition section that acquires an image that has been captured by an imaging optical system that receives reflected light, and includes an image of an object, the reflected light being light that has been applied to the object, and reflected by the object, an angle-of-view information acquisition section that acquires angle-of-view information that indicates an angle of view of the imaging optical system when the image has been captured, and an automatic exposure control section that performs an automatic exposure control process based on the acquired angle-of-view information.

34 Claims, 13 Drawing Sheets

(52) U.S. Cl.
CPC ............. *A61B 1/06* (2013.01); *G02B 23/2469* (2013.01); *H04N 5/217* (2013.01); *A61B 1/00059* (2013.01)

(56) References Cited

U.S. PATENT DOCUMENTS

2011/0279915 A1    11/2011    Mizusawa
2014/0046131 A1    2/2014    Morita et al.

FOREIGN PATENT DOCUMENTS

| JP | 07-89178 | B2 | 9/1995 |
| JP | 10-239740 | A | 9/1998 |
| JP | 2001-258823 | A | 9/2001 |
| JP | 2005-124755 | A | 5/2005 |
| JP | 2007-014695 | A | 1/2007 |
| JP | 2009-219719 | A | 10/2009 |
| JP | 2010-169792 | A | 8/2010 |
| JP | 2011-010131 | A | 1/2011 |

OTHER PUBLICATIONS

International Search Report (ISR) dated Aug. 28, 2012 (and English translation thereof) in International Application No. PCT/JP2012/063594.

* cited by examiner

AUTOMATIC EXPOSURE CONTROL DEVICE, CONTROL DEVICE, ENDOSCOPE DEVICE AND AUTOMATIC EXPOSURE CONTROL METHOD

CROSS REFERENCE TO RELATED APPLICATION

This application is a continuation of International Patent Application No. PCT/JP2012/063594, having an international filing date of May 28, 2012, which designated the United States, the entirety of which is incorporated herein by reference. Japanese Patent Application No. 2011-183593 filed on Aug. 25, 2011 is also incorporated herein by reference in its entirety.

BACKGROUND

The present invention relates to an automatic exposure control device, a control device, an endoscope system, an automatic exposure control method, and the like.

An endoscope system has been widely used that applies illumination light to tissue in a body cavity, and allows the user to perform a diagnosis/procedure using an image signal generated from the light reflected by the tissue. The endoscope system (imaging device) may be configured so that an image sensor (e.g., CCD image sensor or CMOS image sensor) and an objective lens that optically forms an object image on the image sensor are provided on the end of the insertion section. A wide-angle objective lens is normally used as the objective lens of the endoscope in order to prevent a situation in which a lesion area is missed. For example, the viewing angle of a normal endoscope is about 140°.

JP-A-2010-169792 discloses an objective lens that makes it possible to simultaneously observe the object within the front field of view and the object within the side field of view in order to observe the object over a wider range.

An endoscope system is normally provided with a function of automatically adjusting the intensity of illumination light (i.e., dimming function) in order to acquire an object image having a brightness appropriate for observation using such an imaging optical system.

SUMMARY

According to one aspect of the invention, there is provided an automatic exposure control device comprising:

an image acquisition section that acquires an image that has been captured by an imaging optical system that receives reflected light, and includes an image of an object, the reflected light being light that has been applied to the object, and reflected by the object;

an angle-of-view information acquisition section that acquires angle-of-view information that indicates an angle of view of the imaging optical system when the image has been captured; and an automatic exposure control section that performs an automatic exposure control process that controls automatic exposure based on the acquired angle-of-view information.

According to another aspect of the invention, there is provided an endoscope system comprising:

a light source section that emits light that is applied to an object;

an imaging section that captures an image including an image of the object using an imaging optical system that receives reflected light, the reflected light being the light that has been applied to the object, and reflected by the object;

an angle-of-view information acquisition section that acquires angle-of-view information that indicates an angle of view of the imaging optical system when the image has been captured; and an automatic exposure control section that performs an automatic exposure control process that controls that controls automatic exposure based on the acquired angle-of-view information, the automatic exposure control section including an automatic exposure area setting section that sets an automatic exposure area having a size corresponding to the angle-of-view information within the image, and the automatic exposure control section calculating an automatic exposure evaluation value for evaluating an exposure state within the image based on pixel values of pixels within the automatic exposure area, and performing the automatic exposure control process based on the calculated automatic exposure evaluation value.

According to another aspect of the invention, there is provided an automatic exposure control method comprising:

acquiring an image that has been captured by an imaging optical system that receives reflected light, and includes an image of an object, the reflected light being light that has been applied to the object, and reflected by the object;

acquiring angle-of-view information that indicates an angle of view of the imaging optical system when the image has been captured;

setting an automatic exposure area having a size corresponding to the angle-of-view information within the image;

calculating an automatic exposure evaluation value for evaluating an exposure state within the image based on pixel values of pixels within the automatic exposure area; and performing an automatic exposure control process that controls automatic exposure based on the calculated automatic exposure evaluation value.

DESCRIPTION OF EXEMPLARY EMBODIMENTS

Several embodiments of the invention may provide an automatic exposure control device, a control device, an endoscope system, an automatic exposure control method, and the like that make it possible to implement an appropriate exposure control process over the field-of-view range.

According to one embodiment of the invention, there is provided an automatic exposure control device comprising:

an image acquisition section that acquires an image that has been captured by an imaging optical system that receives reflected light, and includes an image of an object, the reflected light being light that has been applied to the object, and reflected by the object;

an angle-of-view information acquisition section that acquires angle-of-view information that indicates an angle of view of the imaging optical system when the image has been captured; and an automatic exposure control section that performs an automatic exposure control process that controls automatic exposure based on the acquired angle-of-view information.

According to one embodiment of the invention, an image (captured image) captured by the imaging optical system is acquired, the angle-of-view information when the captured image has been captured is acquired, and the automatic exposure control process is performed based on the angle-of-view information. This makes it possible to appropriately control the exposure in the field-of-view range. For example, even when using a wide-angle imaging optical system, it is possible to appropriately control the exposure in the wide-angle field-of-view range.

Description of Exemplary Embodiments

Exemplary embodiments of the invention are described below. Note that the following exemplary embodiments do not in any way limit the scope of the invention laid out in the claims. Note also that all of the elements described below in connection with the following exemplary embodiments should not necessarily be taken as essential elements of the invention.

1. Outline

Figure 1:
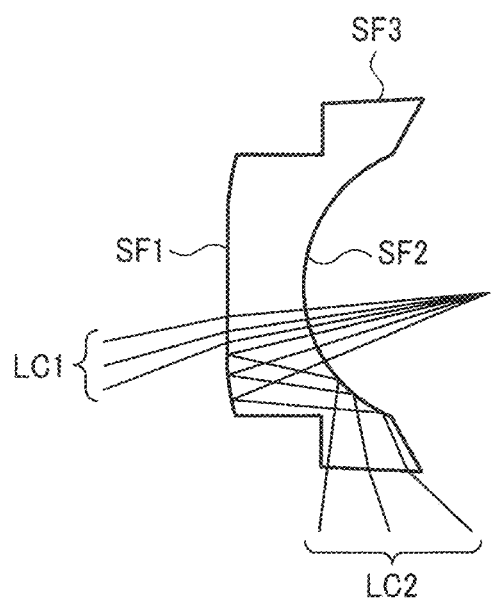
FIG. 1 illustrates a detailed configuration example of an objective lens.

An outline of several embodiments of the invention is described below. FIG. 1 illustrates a configuration example of an objective optical system according to several embodiments of the invention. As illustrated in FIG. 1, a light beam LC1 from the front field of view enters through a surface SF1, and a light beam LC2 from the side field of view enters through a surface SF3. The light beams LC1 and LC2 are refracted or reflected by the surfaces SF1 and SF2, and guided to an imaging optical system, so that the front field of view and the side field of view can be observed. It is possible to provide an endoscope system that allows the user to observe a wide range inside a body cavity as compared with a normal endoscope system by utilizing such an objective optical system.

The difference between an image obtained by such a wide-field endoscope that enables observation over a wide range and an image obtained by a normal endoscope is described below with reference to FIGS. 2A to 2D.

Figure 2B:
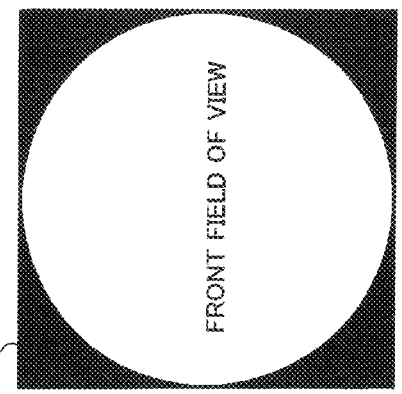
FIGS. 2A to 2D illustrate the difference between an image obtained by a normal endoscope and an image obtained by a wide-field endoscope.
Figure 2D:
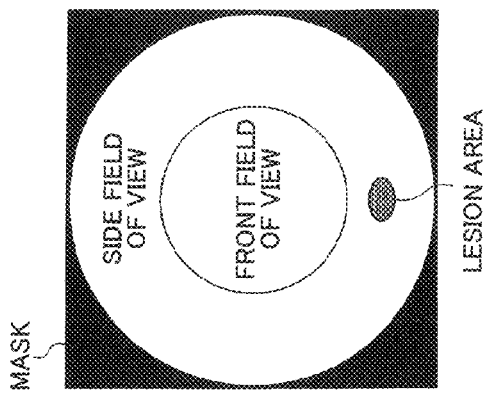
Figure 2A:
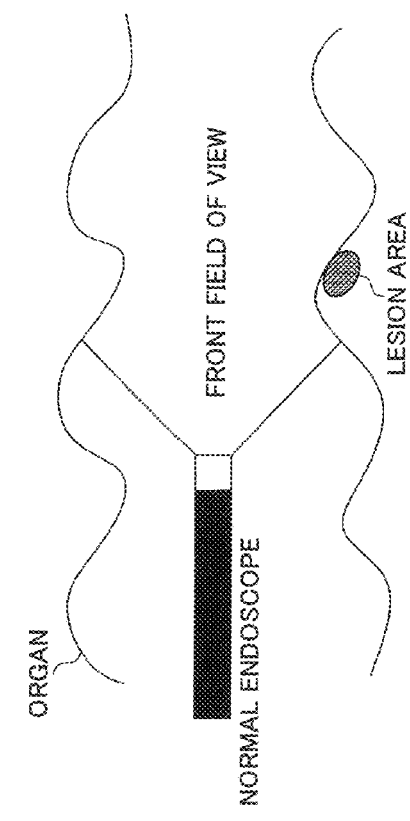

When screening a lesion area that may be present in a hollow tubular organ, the organ is observed while inserting or withdrawing the insertion section of the endoscope, and a lesion area that is positioned on the wall surface of the organ is hidden behind folds or the like (see FIG. 2A). Therefore, the lesion area cannot be observed within the image obtained by the normal endoscope, and may be missed (see FIG. 2B).

Figure 2C:
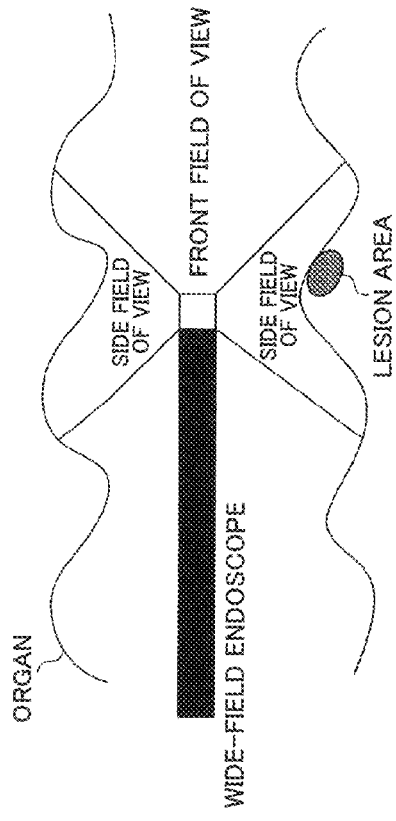

When screening a lesion area using the wide-field endoscope, a lesion area that is positioned on the back side of folds can be observed within the side field of view (see FIG. 2C). Therefore, the lesion area can be observed within the captured image (see FIG. 2D).

An endoscope system is normally provided with a dimming function for adjusting the brightness of the image to improve visibility. The dimming function has been normally designed to implement an endoscope having a normal angle of view (e.g., 140°) based on the pixel values within the front field of view. Therefore, an endoscope that utilizes the above objective optical system may have a problem in that the intensity of light sufficient for observation cannot obtained for the side field of view, and its wide field of view cannot be sufficiently utilized. Moreover, since the distance between the endoscope and the object within the side field of view decreases during screening or the like, blown out highlights may occur within the side field of view, and the lesion area may be missed.

JP-A-2007-14695 discloses a technique that selectively implements a manual dimming process or an automatic dimming process depending on the connected endoscope. However, since the dimming target field of view cannot be changed corresponding to each endoscope when using the method disclosed in JP-A-2007-14695, it is difficult to implement an appropriate dimming process for the side field of view. The above problem may be solved by allowing the user to manually determine and change (switch) the dimming target corresponding to the endoscope used for observation. According to this method, however, the operation becomes complex, and the burden imposed on the user increases.

Figure 3:
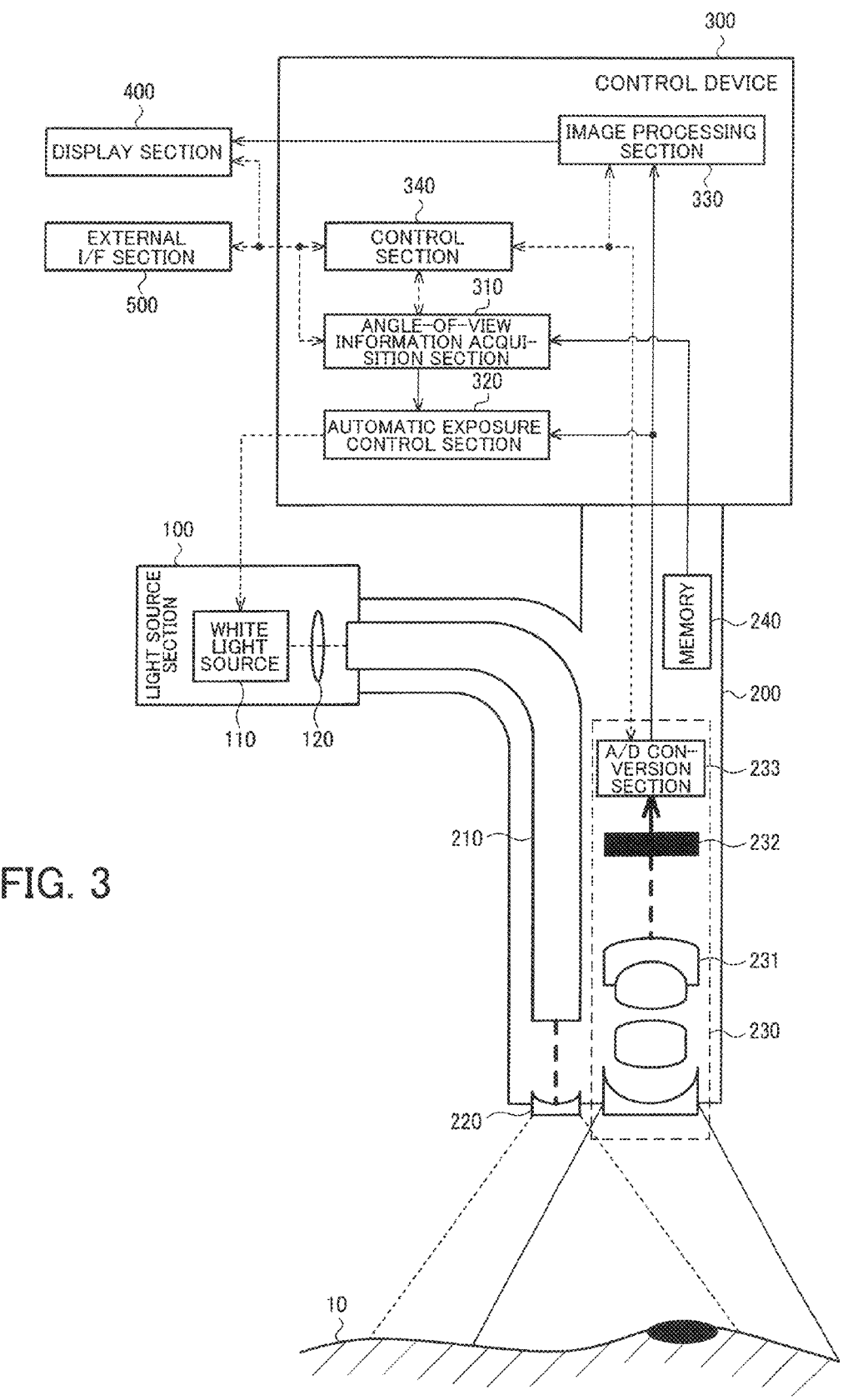
FIG. 3 illustrates a configuration example of an endoscope system according to a first embodiment.

According to several embodiments of the invention, angle-of-view information is acquired based on a scope ID or the like stored in a memory 240, for example (see FIG. 3). An automatic exposure area is set based on the angle-of-view information, and an automatic exposure control process that controls automatic exposure is performed on the automatic exposure area (i.e., exposure control target area). The above configuration makes it possible to control an image within the side field of view to have an appropriate brightness when using a wide-field endoscope that enables observation within the side field of view. Moreover, since the exposure control process can be automatically performed corresponding to the angle-of-view information, the burden imposed on the user due to operation can be reduced.

2. First Embodiment

2.1. Endoscope System

A first embodiment of the invention is described in detail below. FIG. 3 illustrates a configuration example of an endoscope system according to the first embodiment. The endoscope system includes a light source section 100, an insertion section 200, a control device 300 (signal processing section), a display section 400, and an external I/F section 500.

The light source section 100 includes a white light source 110 and a condenser lens 120. The white light source 110 emits white light. The condenser lens 120 focuses the white light emitted from the white light source 110 on a light guide fiber 210 (described below).

The insertion section 200 is formed to be elongated and flexible (i.e., can be curved) so that the insertion section 200 can be inserted into a body cavity or the like. The insertion section 200 includes the light guide fiber 210, an illumination lens 220, an imaging section 230, and a memory 240. The imaging section 230 includes an objective lens 231, an image sensor 232, and an A/D conversion section 233.

The light guide fiber 210 guides the light focused by the light source section 100 to the end of the insertion section 200. The illumination lens 220 diffuses the light guided by the light guide fiber 210, and applies the diffused light to an observation target (object) 10. The objective lens 231 focuses reflected light from the observation target on the image sensor 232. The image sensor 232 outputs analog signals based on the detected reflected light to the A/D conversion section 233. The A/D conversion section 233 converts the analog signals output from the image sensor 232 into digital signals, and outputs the resulting image to the control device 300 as an endoscopic image based on a control signal output from a control section 340 (described later). The memory 240 stores a scope ID assigned to the insertion section 200. The memory 240 is connected to an angle-of-view information acquisition section 310 (described later).

Note that the insertion section 200 is hereinafter appropriately referred to as "scope" for convenience of description. A different scope is used for endoscopic diagnosis depending on the diagnosis target site (e.g., upper gastrointestinal tract or lower gastrointestinal tract). An identification number that specifies the diagnosis target site and a function (e.g., zoom function) is assigned to each scope. The identification number is referred herein as "scope ID".

Figures 4, 5:
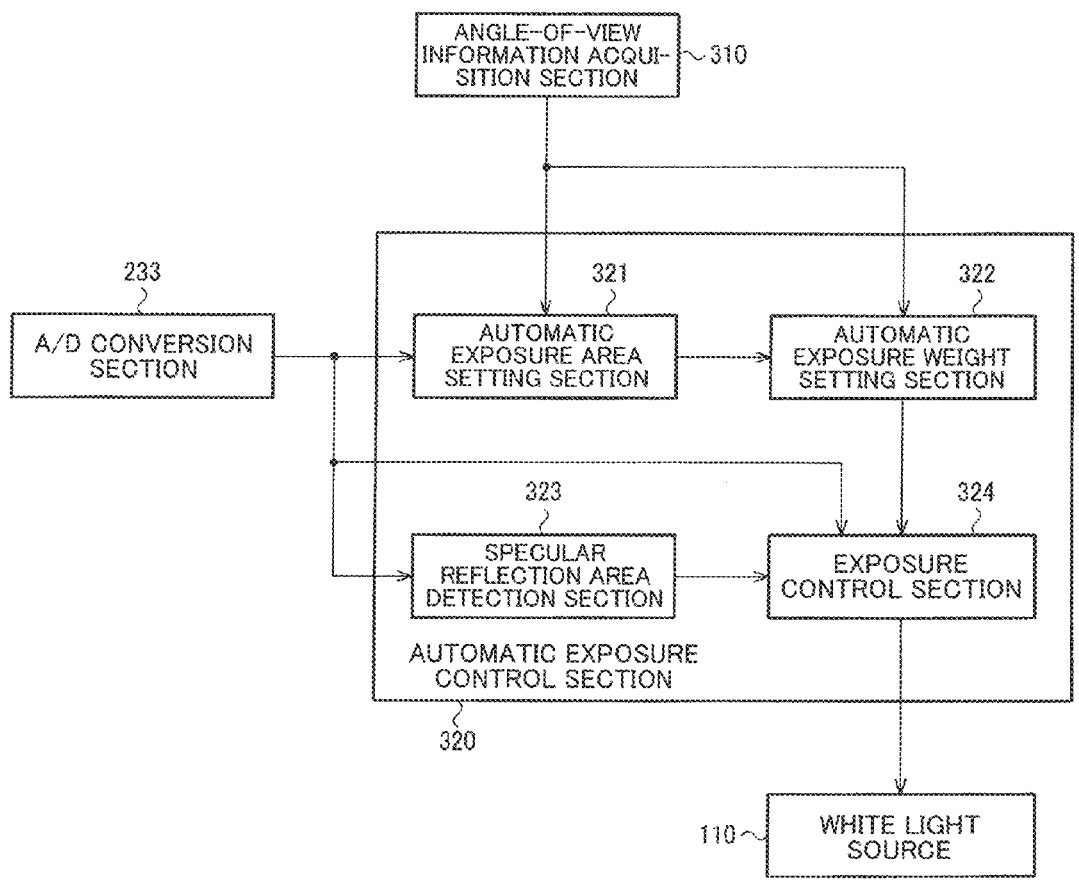
FIG. 4 illustrates an example of a Bayer pixel array.
FIG. 5 illustrates a detailed configuration example of an automatic exposure control section.

The image sensor 232 has a primary color Bayer array, and the endoscopic image obtained by the image sensor 232 is a primary color Bayer image. As illustrated in FIG. 4, the primary color Bayer image is an image in which each pixel has an R, G, or B signal, and the RGB pixels are arranged in a staggered pattern.

The control device 300 includes the angle-of-view information acquisition section 310, an automatic exposure control section 320, an image processing section 330, and the control section 340. The endoscopic image acquired by the imaging section 230 is output to the automatic exposure control section 320 and the image processing section 330. The angle-of-view information acquisition section 310 is connected to the automatic exposure control section 320. The automatic exposure control section 320 is connected to the white light source 110, and controls the white light source 110. The image processing section 330 is connected to the display section 400. The control section 340 is bidirectionally connected to the imaging section 230, the angle-of-view information acquisition section 310, the image processing section 330, the display section 400, and the external I/F section 500, and controls the imaging section 230, the angle-of-view information acquisition section 310, the image processing section 330, the display section 400, and the external I/F section 500.

The angle-of-view information acquisition section 310 acquires angle-of-view information about the scope based on the scope ID stored in the memory 240. Note that the term "angle-of-view information" used herein refers to information that indicates the angle of view of the scope that corresponds to the scope ID, and indicates the maximum angle of view of the imaging optical system included in the scope. The acquired angle-of-view information is output to the automatic exposure control section 320.

The automatic exposure control section 320 controls the intensity of the white light emitted from the white light source 110 based on the angle-of-view information acquired by the angle-of-view information acquisition section 310 so that the pixel value of the endoscopic image acquired by the imaging section 230 is suitable for observation. Note that the process that controls the intensity of the white light emitted from the white light source 110 is hereinafter referred to as "dimming control process (or dimming process)".

The image processing section 330 performs image processing on the endoscopic image acquired (captured) by the imaging section 230. The image processing section 330 performs a tone transformation process and a noise reduction process (described later), for example. The image processing section 330 outputs the resulting image to the display section 400.

The control section 340 is connected to the imaging section 230, the angle-of-view information acquisition section 310, the image processing section 330, the display section 400, and the external I/F section 500, and controls the imaging section 230, the angle-of-view information acquisition section 310, the image processing section 330, the display section 400, and the external I/F section 500.

The display section 400 displays the endoscopic image output from the image processing section 330 on an image display device (e.g., endoscope monitor).

The external I/F section 500 is an interface that allows the user to input information to the endoscope system, for example. The external I/F section 500 includes a power switch (power ON/OFF switch), a shutter button (imaging operation start button), a mode (e.g., imaging mode) switch button, and the like.

Note that the endoscopic image is not limited to a primary color Bayer image. The endoscopic image may be an image acquired by an endoscopic imaging method (e.g., complementary-color imaging method or frame-sequential imaging method) other than the primary color Bayer method.

2.2. Automatic Exposure Control Section

FIG. 5 illustrates a detailed configuration example of the automatic exposure control section 320. The automatic exposure control section 320 includes an automatic exposure area setting section 321, an automatic exposure weight setting section 322, a specular reflection area detection section 323, and an exposure control section 324.

The angle-of-view information acquired by the angle-of-view information acquisition section 310 is output to the automatic exposure area setting section 321 and the automatic exposure weight setting section 322. The endoscopic image acquired by the imaging section 230 is output to the automatic exposure area setting section 321, the specular reflection area detection section 323, and the exposure control section 324. The automatic exposure area setting section 321 is connected to the automatic exposure weight setting section 322. The automatic exposure weight setting section 322 is connected to the exposure control section 324. The specular reflection area detection section 323 is connected to the exposure control section 324. The exposure control section 324 is connected to the white light source 110.

The automatic exposure area setting section 321 sets an automatic exposure area within the endoscopic image acquired by the imaging section 230 based on the angle-of-view information acquired by the angle-of-view information acquisition section 310, and outputs information about the automatic exposure area to the exposure control section 324.

The automatic exposure weight setting section 322 sets an automatic exposure weight to each pixel of the automatic exposure area set by the automatic exposure area setting section 321 based on the angle-of-view information acquired by the angle-of-view information acquisition section 310, and outputs the automatic exposure weight to the exposure control section 324.

The specular reflection area detection section 323 detects a specular reflection area within the endoscopic image based on the pixel values of the endoscopic image acquired by the imaging section 230, and outputs information about the detected specular reflection area to the exposure control section 324.

The exposure control section 324 performs a dimming control process based on the pixel values of the endoscopic image acquired by the imaging section 230, the automatic exposure weight set by the automatic exposure weight setting section 322, and the specular reflection area detected by the specular reflection area detection section 323. The details of these sections (elements) are described later.

2.3. Automatic Exposure Area Setting Section

Figure 6:
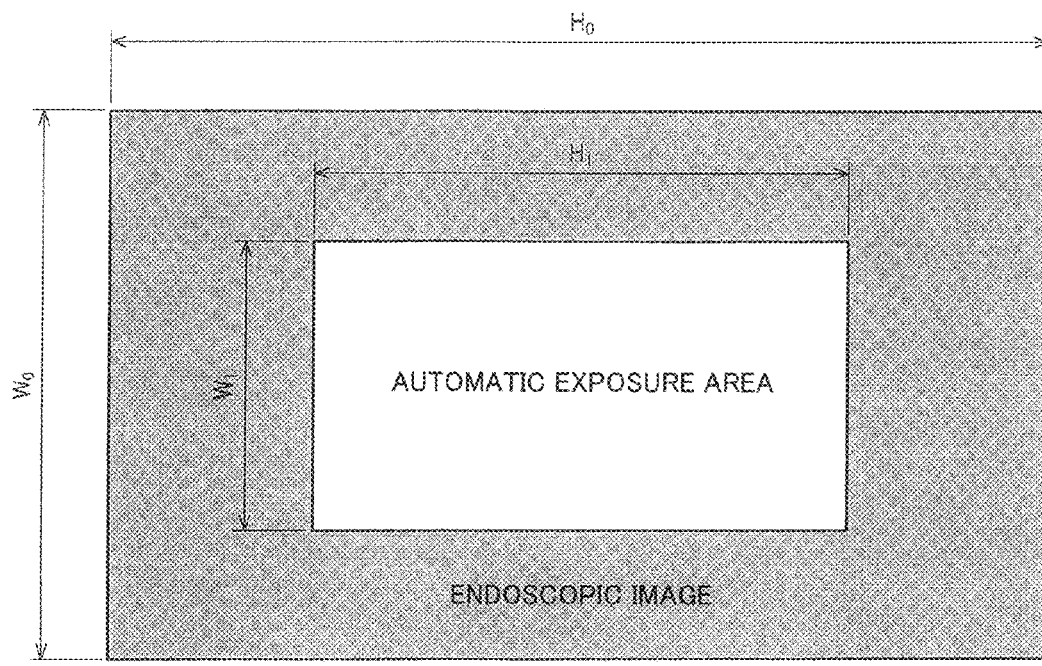
FIG. 6 illustrates an automatic exposure area setting example.

The process performed by the automatic exposure area setting section 321 is described in detail below. FIG. 6 illustrates an automatic exposure area setting example. In the first embodiment, the center of the endoscopic image and the center of the automatic exposure area coincide with each other. The width and the height of the endoscopic image are respectively referred to as $W_0$ and $H_0$, and the width and the height of the automatic exposure area are respectively referred to as $W_1$ and $H_1$. The following expression (1) shows the relationship between $W_0$ and $W_1$, and the following expression (2) shows the relationship between $H_0$ and $H_1$.

$$W_1 = \alpha_0 W_0 \tag{1}$$

$$H_1 = \alpha_0 H_0 \tag{2}$$

Figure 7:
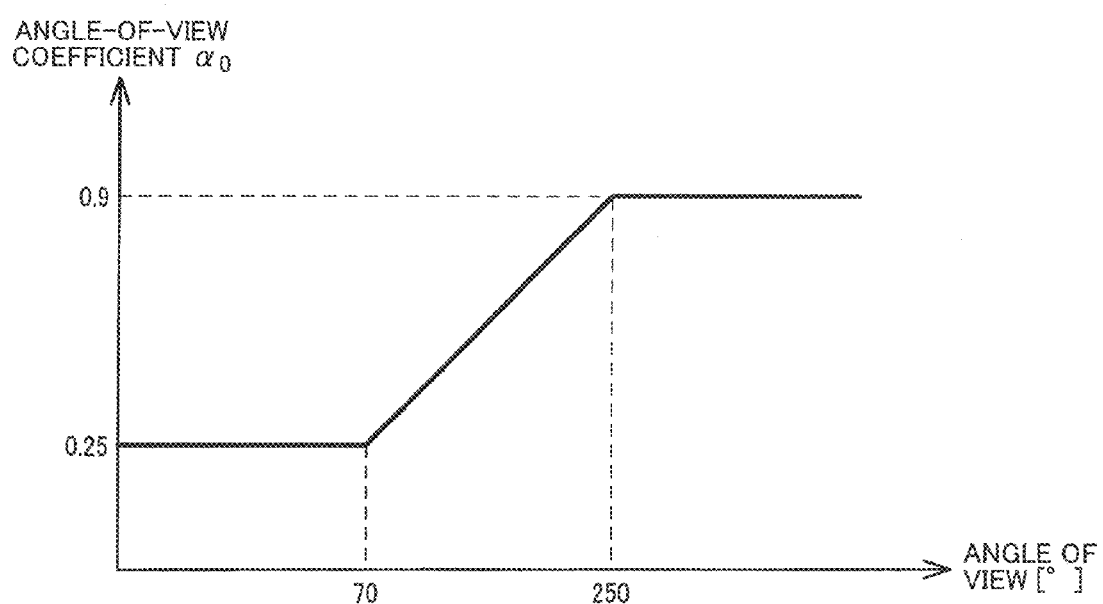
FIG. 7 illustrates an angle-of-view coefficient setting example.

Note that $\alpha_0$ is an angle-of-view coefficient within the range of 0.0 to 1.0 that is determined based on the angle-of-view information. FIG. 7 illustrates an angle-of-view coefficient ($\alpha_0$) setting example. When the user desires to observe the side field of view, a wide-field endoscope having a wide maximum angle of view is used (see FIG. 2D). The following description is given on the assumption that the wide-field endoscope has a maximum angle of view equal to or larger than 180°. When the endoscope has an angle of view (field of view) equal to or larger than 180°, and the angle-of-view coefficient $\alpha_0$ is set as illustrated in FIG. 7, the side field of view is included in the automatic exposure area to a larger extent as the maximum angle of view of the scope increases. This makes it possible to implement a dimming process that is more appropriate for observation on the side field of view that is the observation target for the user.

Although an example in which the angle-of-view coefficient $\alpha_0$ is set as illustrated in FIG. 7 has been described above, the configuration is not limited thereto. The angle-of-view coefficient $\alpha_0$ may be arbitrarily set as long as the angle-of-view coefficient $\alpha_0$ is set so that the angle-of-view coefficient $\alpha_0$ increases as the maximum angle of view acquired based on the angle-of-view information increases.

Although an example in which the automatic exposure area has a rectangular shape has been described above, the configuration is not limited thereto. For example, the automatic exposure area may have a circular shape.

2.4. Automatic Exposure Weight Setting Section

The process performed by the automatic exposure weight setting section 322 is described in detail below. The automatic exposure weight setting section 322 sets an automatic exposure weight within the range of 0.0 to 1.0 to each pixel included in the automatic exposure area based on the angle-of-view information.

Specifically, when the endoscope has a normal maximum angle of view (e.g., about 140°), the automatic exposure weight setting section 322 sets the automatic exposure weight to 1.0 over the entire automatic exposure area. In this case, the exposure control section 324 performs the dimming process based on the average value or the sum of the pixel values of the automatic exposure area.

Figure 8:
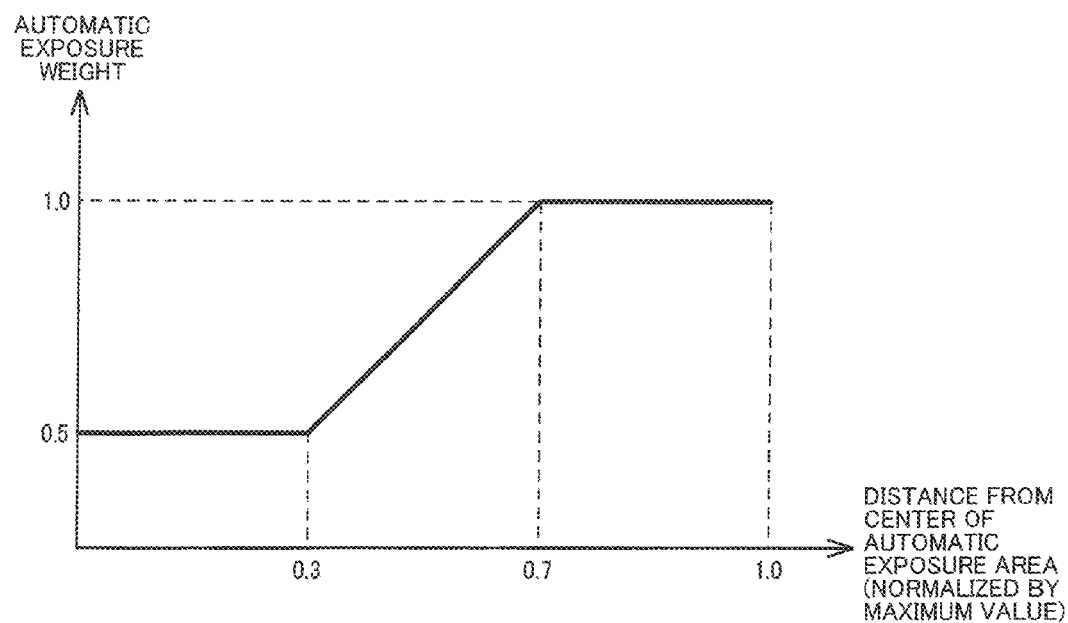
FIG. 8 illustrates an automatic exposure weight setting example for a wide-angle scope.

When the endoscope is a wide-field endoscope that has a maximum angle of view larger than the normal maximum angle of view, the automatic exposure weight setting section 322 sets the automatic exposure weight corresponding to the coordinates of each pixel to each pixel included in the automatic exposure area (see FIG. 8). In the automatic exposure weight setting example illustrated in FIG. 8, the automatic exposure weight is set corresponding to the distance from the center of the automatic exposure area to each pixel. The distance from the center of the automatic exposure area is calculated by the following expression (3).

$$D(p, q) = \max\left(\frac{|p - W_0/2|}{W_1/2}, \frac{|q - H_0/2|}{H_1/2}\right) \tag{3}$$

where, (p, q) are the coordinates of the pixel to which the automatic exposure weight is set, D(p, q) is the normalized distance from the center of the automatic exposure area to the coordinates (p, q), max( ) is a function that compares the input values, and outputs the maximum value among the input values, $W_0$ and $H_0$ are respectively the width and the height of the endoscopic image, and $W_1$ and $H_1$ are respectively the width and the height of the automatic exposure area. In FIG. 6, the origin (0, 0) of the coordinates (p, q) is situated at the upper left corner of the automatic exposure area, and the center of the automatic exposure area is indicated by ($W_0/2$, $H_0/2$).

As described above with reference to FIG. 2D, the wide-field endoscope is characterized in that it is possible to observe a lesion situated within the side field of view. An endoscopic image in which the side field of view has a brightness appropriate for observation can be acquired by setting a large automatic exposure weight to the pixels within the side field of view as compared with the pixels within the front field of view, as illustrated in FIG. 8. Note that the automatic exposure weight may be set in a way differing from the automatic exposure weight setting example illustrated in FIG. 8. Specifically, the automatic exposure weight may be arbitrarily set as long as a relatively large automatic exposure weight is set to the pixels within the side field of view as compared with the pixels within the front field of view.

2.5. Modified Automatic Exposure Weight Setting Examples

Figure 9:
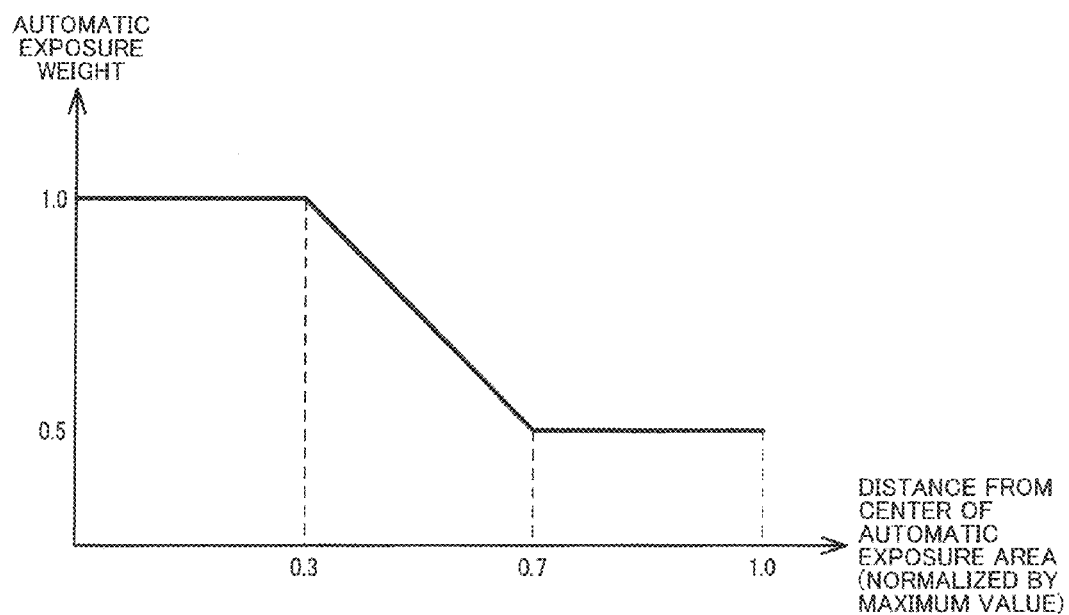
FIG. 9 illustrates a modified automatic exposure weight setting example for a scope having a normal angle of view.

When the endoscope has a normal maximum angle of view, the automatic exposure weight may be set as illustrated in FIG. 9. The dimming process can be implemented so that a brightness appropriate for observation is obtained at the center of the endoscopic image (that coincides with the center of the automatic exposure area in the first embodiment) where the close observation target object is considered to be present by setting the automatic exposure weight as illustrated in FIG. 9.

Figure 10:
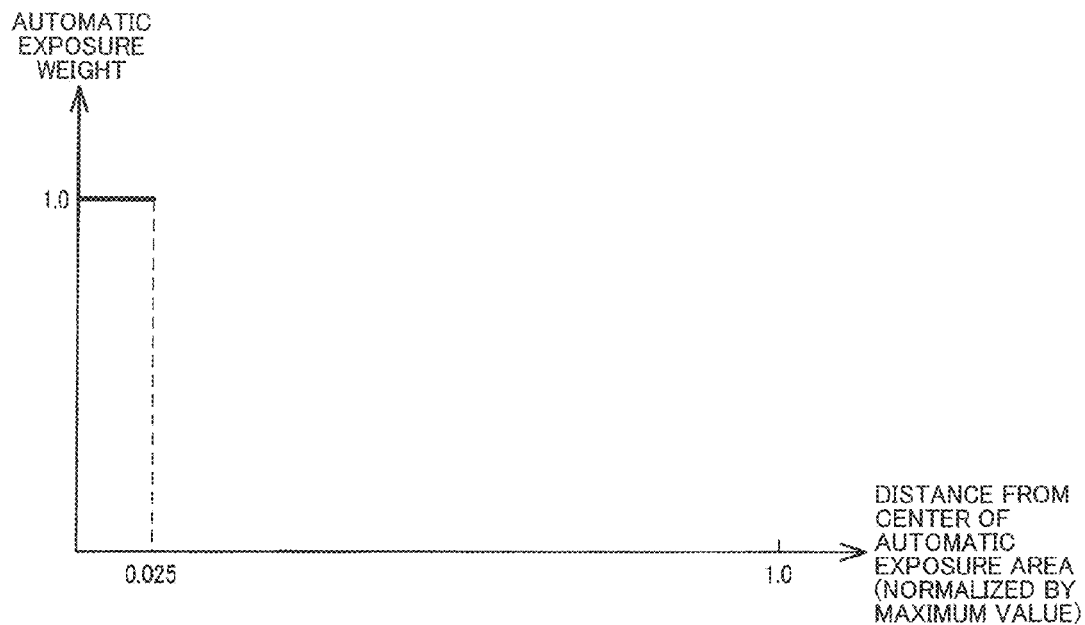
FIG. 10 illustrates a second modified automatic exposure weight setting example for a scope having a normal angle of view.

As illustrated in FIG. 10, when the endoscope has a normal maximum angle of view, the automatic exposure weight may be set to 1.0 in a very narrow area in the vicinity of the center of the automatic exposure area, and may be set to 0.0 in the remaining area. The illumination light that is applied to the close observation target object situated in the vicinity of the center of the endoscopic image can be adjusted to have an intensity that is more appropriate for observation by setting the automatic exposure weight as illustrated in FIG. 10.

Figure 11:
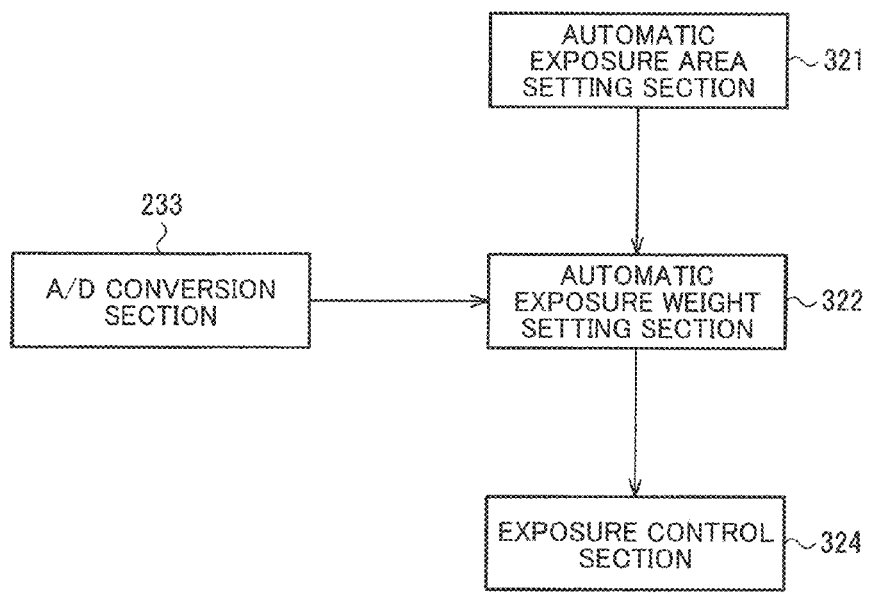
FIG. 11 is a view illustrating a modified automatic exposure weight setting example.

As illustrated in FIG. 11, the automatic exposure weight setting section 322 may receive the endoscopic image acquired by the imaging section 230, and set the automatic exposure weight within the range of 0.0 to 1.0 based on the pixel values of the endoscopic image.

In this case, the automatic exposure weight setting section 322 sets the automatic exposure weight based on the pixel values of a luminance image generated from the endoscopic image that is a primary color Bayer image. Specifically, the automatic exposure weight setting section 322 calculates the pixel value $Y(x, y)$ of the luminance image at the coordinates $(x, y)$ using the following expression (4).

$$Y(x,y)=RAW(x,y)+RAW(x+1,y)+RAW(x,y+1)+RAW(x+1,y+1) \quad (4)$$

where, $RAW(x, y)$ is the pixel value of the endoscopic image at the coordinates $(x, y)$.

The automatic exposure weight setting section 322 sets the automatic exposure weight using the luminance value $Y(x, y)$ (see the following expression (5)).

$$W_L(p,q)=h\{Y(p,q)\}\{(p,q) \in R\} \quad (5)$$

where, $W_L(p, q)$ is the automatic exposure weight at the coordinates $(p, q)$, R is the automatic exposure area, $(p, q) \in R$ indicates that the pixel positioned at the coordinates $(p, q)$ is included in the automatic exposure area, and $h( )$ is a cumulative histogram of the luminance image included in the automatic exposure area. The cumulative histogram indicates the number of pixels that have a pixel value equal to or less than $Y(p, q)$, and are present within the automatic exposure area. The cumulative histogram is normalized to the range of 0.0 to 1.0.

For example, when the automatic exposure weight is set as illustrated in FIG. 10 (spot metering), and a hollow tubular object is observed, since the pixel values within the side field of view that are relatively larger than the pixel values within the front field of view are not used to evaluate the dimming process, the illumination light may be unnecessarily applied to the side field of view, and blown out highlights may occur within the side field of view. When the automatic exposure weight is set as illustrated in FIG. 8, and a protruding object (e.g., polyp) is observed at the center of the front field of view, since the pixel values within the front field of view that are relatively larger than the pixel values within the side field of view are not used to evaluate the dimming process, the illumination light may be unnecessarily applied to the front field of view, and blown out highlights may occur within the front field of view.

According to the above modification, it is possible to set a large automatic exposure weight to a pixel having a large pixel value by setting the automatic exposure weight based on the cumulative histogram. Therefore, the dimming process can be performed, and blown out highlights can be suppressed independently of the shape of the object based on the pixel values within an area of the automatic exposure area to which the illumination light is strongly applied.

2.6. Specular Reflection Area Detection Section

The process performed by the specular reflection area detection section 323 is described in detail below. The specular reflection area detection section 323 extracts an area having a pixel value equal to or larger than a given luminance threshold value from the luminance image obtained using the expression (4). Specifically, the specular reflection area detection section 323 extracts a specular reflection area and a blown out highlight area.

The term "specular reflection area" used herein refers to an area in which the illumination light applied to the object from the illumination lens 220 is specularly reflected by the object, and forms an image on the image sensor 232. The term "blown out highlight area" used herein refers to an area in which the illumination light is not specularly reflected, but is strongly reflected so that the intensity of the reflected light exceeds the upper limit that can be detected by the image sensor 232.

Since the blown out highlight area includes the illumination light that is diffusely reflected by the surface of the object, the pixel values in an area around the blown out highlight area are large. The specular reflection area is an area in which the angle at which the illumination light is incident on the surface of the object coincides with the reflection angle. Since the incident angle and the reflection angle do not coincide with each other in an area around the specular reflection area, the difference in pixel value is large between the specular reflection area and an area around the specular reflection area. Specifically, the pixel values in an area around the specular reflection area are smaller than the pixel values in an area around the blown out highlight area.

Therefore, the specular reflection area detection section 323 determines whether the extracted area is the specular reflection area or the blown out highlight area based on the pixel values in an area around the extracted area. Specifically, the specular reflection area detection section 323 extracts an area in which the pixel values are saturated (e.g., an area in which the pixel values are equal to or larger than a threshold value), assigns a label to the extracted (saturated) area, and calculates the average pixel value of peripheral pixels corresponding to each labeled area to which an identical label is assigned. The peripheral pixels refer to pixels that are adjacent to the extracted labeled area. The specular reflection area detection section 323 compares the average pixel value of the peripheral pixels calculated corresponding to each labeled area with a given peripheral threshold value, and determines the labeled area to be the specular reflection area when the average pixel value of the peripheral pixels is less than the peripheral threshold value.

2.7. Automatic Exposure Control Section

The process performed by the exposure control section 324 is described in detail below. The exposure control section 324 generates the luminance image using the expression (4) based on the endoscopic image. The exposure control section 324 calculates an automatic exposure evaluation value V based on the following expression (6), and performs a dimming control process based on the calculated automatic exposure evaluation value V and a given automatic exposure target value.

$$V = \frac{\sum_{\substack{(p,q) \in R \\ (p,q) \notin M}} Y(p,q) \cdot W_L(p,q)}{\sum_{\substack{(p,q) \in R \\ (p,q) \notin M}} W_L(p,q)} \quad (6)$$

where, (p, q) are the coordinates of the endoscopic image, $W_L(p, q)$ is the automatic exposure weight at the coordinates (p, q), and M is the specular reflection area. The following expression (7) indicates that the pixel positioned at the coordinates (p, q) is not included in the specular reflection area.

$$(p,q) \notin M \quad (7)$$

The exposure control section 324 maintains the current dimming process when the absolute difference value between the calculated automatic exposure evaluation value and the automatic exposure target value is less than a given threshold value. When the absolute difference value is equal to or larger than the given threshold value, the exposure control section 324 performs the dimming process at a constant change ratio within a given period so that the automatic exposure evaluation value coincides with the automatic exposure target value after the lapse of the given period.

2.8. Modified Automatic Exposure Evaluation Value Setting Example

Although an example in which the weighted average value of the pixel values of the luminance image is used as the automatic exposure evaluation value has been described above, the configuration is not limited thereto. For example, a weighted product sum of the pixel values of the luminance image may be used as the automatic exposure evaluation value.

In the first embodiment, the automatic exposure evaluation value V may be calculated by the following expression (8). It is possible to reduce the occurrence frequency of blown out highlights that are undesirable for the endoscopic image by performing the dimming process based on the maximum luminance value.

$$V = \max_{\substack{(p,q) \in R \\ (p,q) \notin M}} \{Y(p,q)\} \quad (8)$$

In the first embodiment, the automatic exposure evaluation value may be calculated from all of the pixels that are included in the automatic exposure area, and are not included in the specular reflection area, or may be calculated from pixels that are selected by thinning out (at given intervals) the pixels that are included in the automatic exposure area, and are not included in the specular reflection area. The amount of calculations can be reduced by calculating the automatic exposure target value after thinning out the pixels.

Although an example in which the automatic exposure evaluation value is calculated based on the pixel values of the luminance image has been described above, the configuration is not limited thereto. For example, the automatic exposure evaluation value may be calculated based on the pixel values of the endoscopic image.

In the first embodiment, the endoscopic image is the primary color Bayer image illustrated in FIG. 4, and each pixel of the endoscopic image has the R, G, or B signal. The automatic exposure evaluation value may be calculated using only the R, G, or B signals. In this case, since each pixel has only the R, or B signal, the signals may be interpolated on a pixel basis using a known interpolation process, and the automatic exposure evaluation value may be calculated using the interpolated signals. Note that the automatic exposure evaluation value may be calculated from the pixels having only the R, G, or B signal.

2.9. Modified Automatic Exposure Target Value Setting Example

Although an example in which the automatic exposure evaluation value is calculated based on the angle-of-view information, and the dimming process is performed using the calculated automatic exposure target value has been described above, the configuration is not limited thereto. For example, the automatic exposure evaluation value may not be calculated based on the angle-of-view information, and the automatic exposure target value may be changed corresponding to the angle-of-view information. For example, when the endoscope is a wide-field endoscope, the automatic exposure target value may be set to half of the automatic exposure target value used for a normal endoscope.

As described above with reference to FIG. 2C, the distance between the wide-field endoscope and the object may differ to a large extent in the front field of view or the side field of view. Therefore, if the automatic exposure target value is not changed when using the wide-field endoscope, blown out highlights may occur in the front field of view or the side field of view. For example, since the distance between the end of the endoscope and the object is short in the side field of view when observing a hollow tubular object, the side field of view tends to be brightly illuminated, and blown out highlights tend to occur in the side field of view.

According to the above modification, it is possible to reduce the occurrence frequency of blown out highlights in the side field of view of the wide-field endoscope by setting the automatic exposure target value for the wide-field endoscope to be smaller than the automatic exposure target value used for a normal endoscope.

Note that the automatic exposure target value for the wide-field endoscope need not necessarily be set to half of the automatic exposure target value used for a normal endoscope. The automatic exposure target value for the wide-field endoscope may be arbitrarily set as long as the automatic exposure target value is set so that the automatic exposure target value decreases as the angle of view of the endoscope increases.

Figure 12:
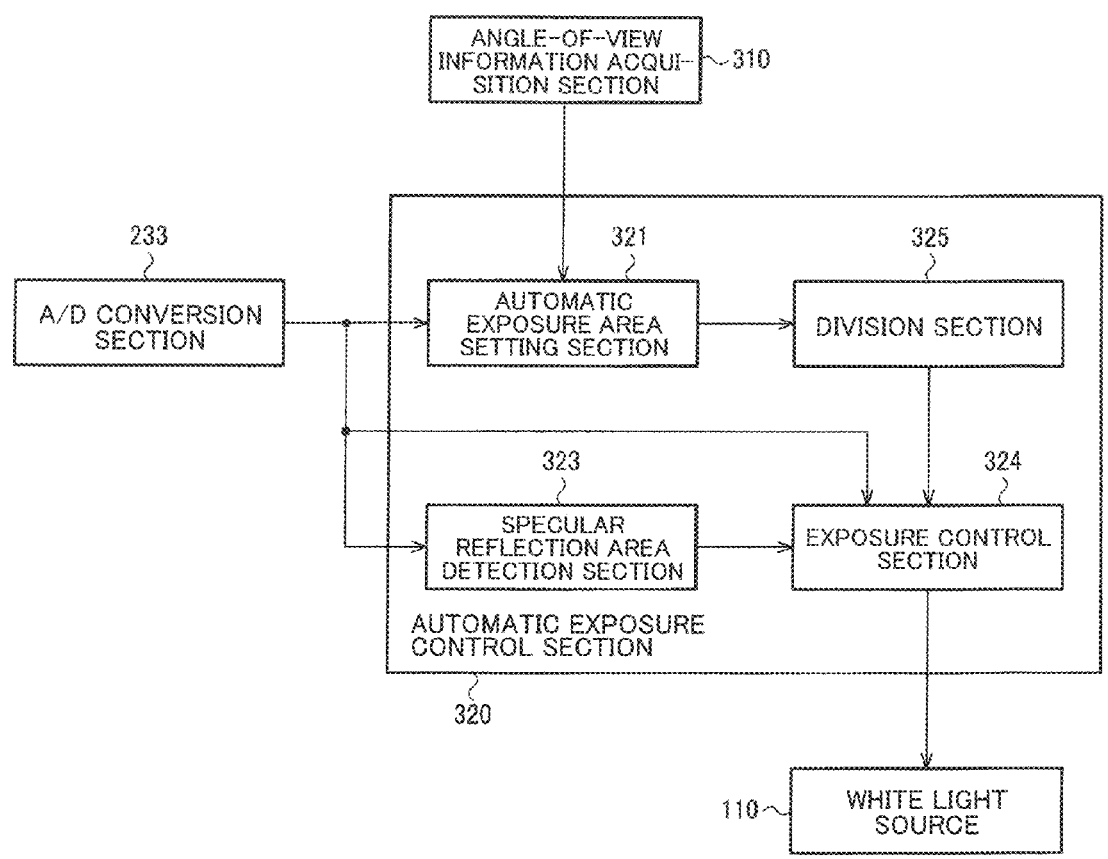
FIG. 12 illustrates a first modified configuration example of an automatic exposure control section.

2.10. First Modified Configuration Example of Automatic Exposure Control Section FIG. 12 illustrates a first modified configuration example of the automatic exposure control section 320. The automatic exposure control section 320 illustrated in FIG. 12 includes an automatic exposure area setting section 321, a specular reflection area detection section 323, an exposure control section 324, and a division section 325.

The automatic exposure area setting section 321 is connected to the division section 325. The division section 325 is connected to the exposure control section 324. The automatic exposure area setting section 321 and the specular reflection area detection section 323 are configured in the same manner as in the configuration example described above with reference to FIG. 5.

Figure 13:
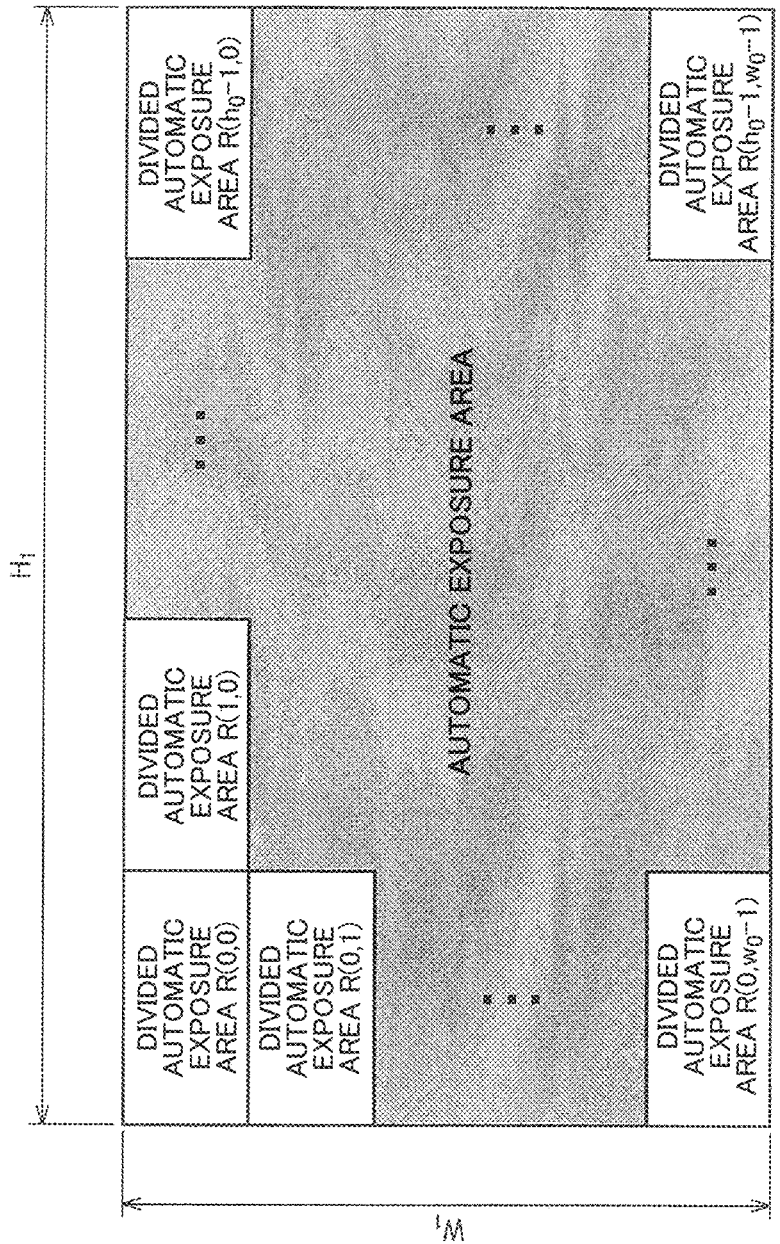
FIG. 13 is a view illustrating a divided automatic exposure area.

As illustrated in FIG. 13, the division section 325 divides the automatic exposure area set by the automatic exposure area setting section 321 into a plurality of divided automatic exposure areas, and outputs information about the divided automatic exposure areas to the exposure control section 324. More specifically, the division section 325 divides the automatic exposure area into $w_0 \times h_0$ ($w_0$ and $h_0$ are natural numbers) divided automatic exposure areas. In FIG. 13, an index is assigned to each divided automatic exposure area for convenience of explanation. Specifically, 0 to $w_0-1$ are used as the indices in the horizontal direction, and 0 to $h_0-1$ are used as the indices in the vertical direction. R(w, h) indicates the divided automatic exposure area to which the index w in the horizontal direction and the index h in the vertical direction are assigned.

The exposure control section 324 performs the dimming control process based on the pixel values of the endoscopic image acquired by the imaging section 230, the divided automatic exposure areas obtained by the division section 325, and the specular reflection area detected by the specular reflection area detection section 323. More specifically, the exposure control section 324 calculates a divided automatic exposure evaluation value of each divided automatic exposure area using the following expression (9).

$$V(w, h) = \underset{\substack{(p,q) \in R(w,h) \\ (p,q) \notin M}}{\text{ave}} \{Y(p, q)\} \quad (9)$$

where, V(w, h) is a divided evaluation value that is the evaluation value of the divided automatic exposure area R(w, h), ave( ) is a function that outputs the average value of the input values, and $(p, q) \in R(w, h)$ indicates that the pixel of the endoscopic image positioned at the coordinates (p, q) is included in the divided automatic exposure area R(w, h).

The exposure control section 324 performs the dimming process based on the calculated divided automatic exposure evaluation value taking account of the brightness balance of the entire image so that the blown out highlight area is not present (e.g., the method disclosed in JP-A-5-313224). Specifically, the exposure control section 324 performs the dimming control process based only on the divided automatic exposure evaluation values that are equal to or larger than a given threshold value. This makes it possible to suppress blown out highlights.

Figure 14:
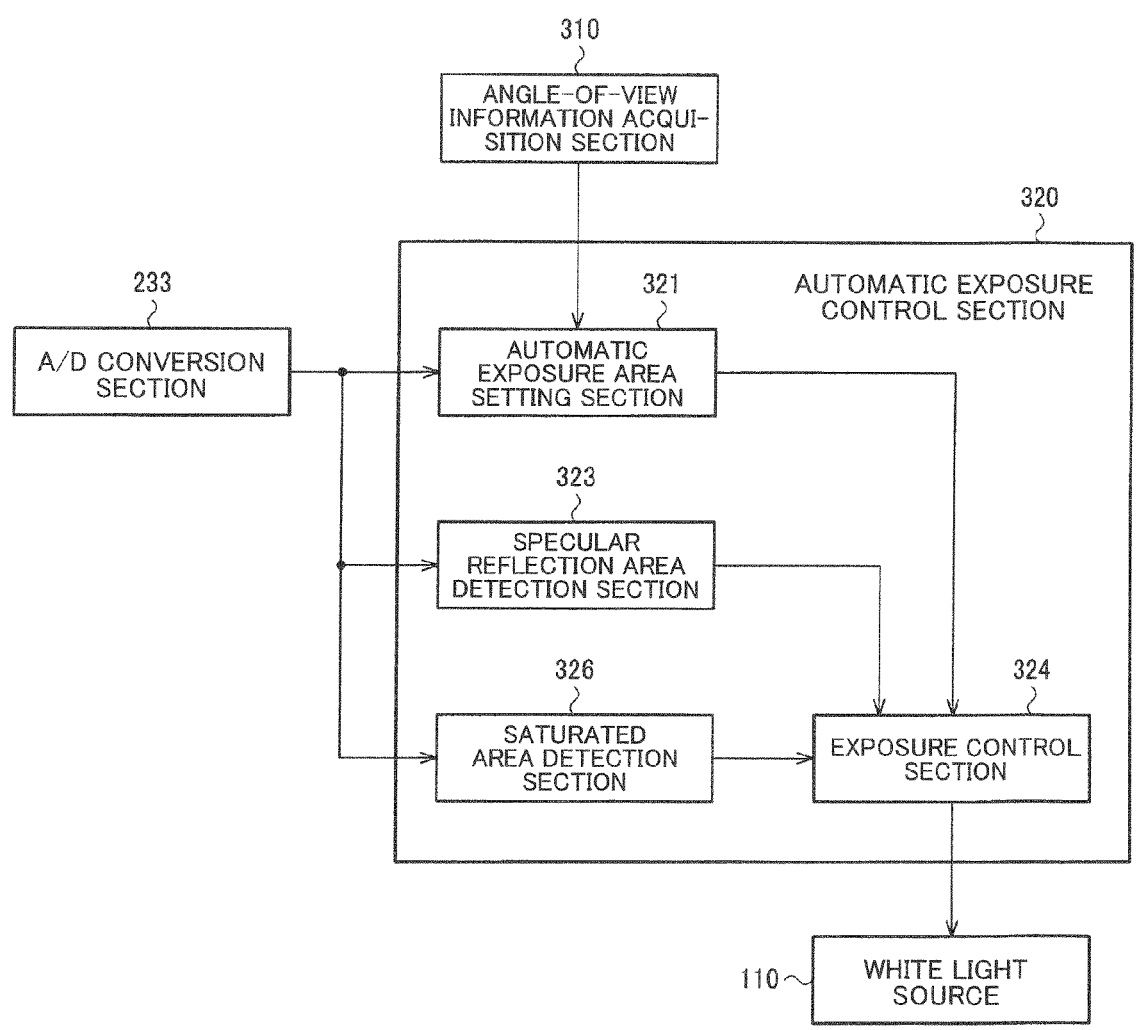
FIG. 14 illustrates a second modified configuration example of an automatic exposure control section.

2.11. Second Modified Configuration Example of Automatic Exposure Control Section FIG. 14 illustrates a second modified configuration example of the automatic exposure control section 320. The automatic exposure control section 320 illustrated in FIG. 14 includes an automatic exposure area setting section 321, a specular reflection area detection section 323, an exposure control section 324, and a saturated area detection section 326.

The endoscopic image acquired by the imaging section 230 is output to the automatic exposure area setting section 321, the specular reflection area detection section 323, and the saturated area detection section 326. The automatic exposure area setting section 321 is connected to the exposure control section 324. The saturated area detection section 326 is connected to the exposure control section 324. The automatic exposure area setting section 321 and the specular reflection area detection section 323 are configured in the same manner as in the configuration example described above with reference to FIG. 5.

The saturated area detection section 326 detects a saturated area from the endoscopic image acquired by the imaging section 230 based on the pixel values of the endoscopic image, and outputs information about the detected saturated area to the exposure control section 324. More specifically, the saturated area detection section 326 detects an area of the luminance image generated from the endoscopic image in which the pixel values are equal to or larger than a given threshold value as the saturated area.

Note that the term "saturated area" used herein refers to an area in which reflected light having an intensity larger than the detection upper limit is focused on the image sensor 232, and the endoscopic image has a constant large pixel value (e.g., the maximum pixel value) regardless of the intensity of the reflected light. The specular reflection area and the blown out highlight area fall under the term "saturated area".

The exposure control section 324 performs the dimming process based on the automatic exposure area set by the automatic exposure area setting section 321, the specular reflection area detected by the specular reflection area detection section 323, and the saturated area detected by the saturated area detection section 326.

Specifically, the exposure control section 324 sets the number of pixels that are included in the automatic exposure area and the blown out highlight area to be the automatic exposure evaluation value. The blown out highlight area is an area obtained by excluding the specular reflection area from the saturated area. The exposure control section 324 performs the dimming process stepwise using the calculated automatic exposure evaluation value. The stepwise dimming process is implemented by controlling the power supplied to the white light source 110 stepwise, for example. When the automatic exposure evaluation value is larger than a given dimming upper limit value, the exposure control section 324 decrements the dimming level by 1 to reduce the intensity of the illumination light applied to the object. When the automatic exposure evaluation value is smaller than a given dimming lower limit, the exposure control section 324 increments the dimming level by 1 to increase the intensity of the illumination light applied to the object. Note that the dimming upper limit value is larger than the dimming lower limit value.

It is possible to minimize the blown out highlight area that is undesirable for observation by performing the above dimming control process. Moreover, the intensity of the illumination light applied to the object within the automatic exposure area can be increased as much as possible while suppressing the blown out highlight area.

2.12. Image Processing Section

Figure 15:
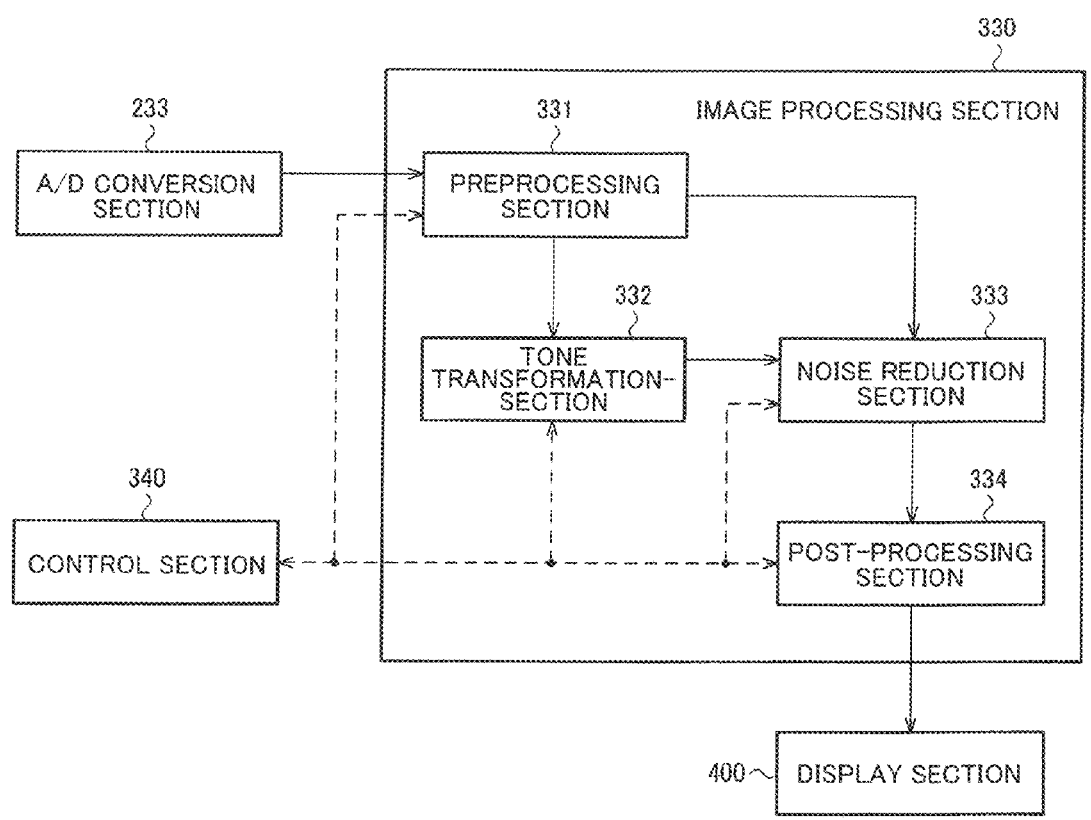
FIG. 15 illustrates a detailed configuration example of an image processing section.

FIG. 15 illustrates a detailed configuration example of the image processing section 330. The image processing section 330 includes a preprocessing section 331, a tone transformation section 332, a noise reduction section 333, and a post-processing section 334.

The endoscopic image acquired by the imaging section 230 is output to the preprocessing section 331. The preprocessing section 331 is connected to the tone transformation section 332 and the noise reduction section 333. The tone transformation section 332 is connected to the noise reduction section 333. The noise reduction section 333 is connected to the post-processing section 334. The post-processing section 334 is connected to the display section 400.

The preprocessing section 331 performs image processing (e.g., white balance process and interpolation process) on the endoscopic image acquired by the imaging section 230, and outputs the resulting endoscopic image to the tone transformation section 332 and the noise reduction section 333.

The tone transformation section 332 performs a tone transformation process on the endoscopic image preprocessed by the preprocessing section 331, and outputs the resulting endoscopic image to the noise reduction section 333. The details of the tone transformation process are described later.

The noise reduction section 333 performs a noise reduction process on the endoscopic image subjected to the tone transformation process based on the pixel values of the endoscopic image before and after the tone transformation process performed by the tone transformation section 332, and outputs the resulting endoscopic image to the post-processing section 334. The details of the noise reduction process are described later.

The post-processing section 334 performs image processing (e.g., color conversion process and contour enhancement process) on the endoscopic image output from the noise reduction section 333, and outputs the resulting endoscopic image to the display section 400.

2.13. Tone Transformation Section

The process performed by the tone transformation section 332 is described in detail below. The tone transformation section 332 performs a space-variant tone transformation process that depends on the position and the tone value of each pixel (e.g., the method disclosed in JP-T-2008-511048).

It is possible to suppress blocked up shadows and blown out highlights that are undesirable for observation while maintaining the local contrast within the endoscopic image by performing such a tone transformation process. As described above with reference to FIG. 2C, the distance between the wide-field endoscope and the object may differ to a large extent in the front field of view and the side field of view. In this case, blown out highlights can be suppressed by the dimming process performed by the automatic exposure control section 320. However, it may be difficult to observe part of the endoscopic image since the intensity of the illumination light is insufficient. Moreover, blown out highlights may not be completely eliminated. The observable area of the endoscopic image can be increased by performing the adaptive tone transformation process on an area in which the intensity of the illumination light is insufficient, or the remaining blown out highlight area.

Note that a space-variant tone transformation process based on local chromatic adaptation that models the visual characteristics of a human being may also be employed.

2.14. Noise Reduction Section

The process performed by the noise reduction section 333 is described in detail below. The noise reduction section 333 performs a filtering process that utilizes a known bilateral filter shown by the following expressions (10) to (12), for example. The noise reduction process is performed by the expressions 9 to 11.

$$S(x, y) = \frac{\sum_{(i,j) \in F} RAW'(x+i, y+j) \cdot W_{diff}(i, j) \cdot W_{dist}(i, j)}{\sum_{(i,j) \in F} W_{diff}(i, j) \cdot W_{dist}(i, j)} \quad (10)$$

$$W_{diff}(i, j) = \exp\left[\frac{-\{RAW(x, y) - RAW'(x+i, y+j)\}^2}{2\sigma_{diff}^2}\right] \quad (11)$$

$$W_{dist}(i, j) = \exp\left\{\frac{-(i^2 + j^2)}{2\sigma_{dist}^2}\right\} \quad (12)$$

where, $S(x, y)$ is the pixel value obtained by performing the noise reduction process on the endoscopic image $RAW'(x, y)$ subjected to the tone transformation process at the coordinates $(x, y)$, F is the bilateral filter application range around the coordinates $(x, y)$, $W_{diff}$ is a weight (i.e., a weight based on the difference in pixel value) when using the pixel values within the bilateral filter application range for the noise reduction process, $\sigma_{diff}$ is a parameter used when calculating the weight $W_{diff}$ based on the difference in pixel value, $W_{dist}$ is a weight (i.e., a weight based on the distance from the coordinates $(x, y)$ to the pixel) when using the pixel values within the bilateral filter application range for the noise reduction process, $\sigma_{dist}$ is a parameter used when calculating the weight $W_{dist}$ based on the distance, $(i, j)$ are indices within the bilateral filter, provided that the indices i and j respectively satisfy $-I_0 \leq i \leq I_0$ and $-J_0 \leq j \leq J_0$, and $I_0$ and $J_0$ are natural numbers. The size of the bilateral filter is $(2 \times I_0 + 1) \times (2 \times J_0 + 1)$. Note that the following description is given on the assumption that $J_0 = I_0$ for convenience of explanation.

The above bilateral filter is configured so that the degree of noise reduction can be adjusted by changing the parameters $\sigma_{diff}$ and $\sigma_{dist}$ and the value $I_0$. Specifically, the degree of noise reduction can be increased by increasing the parameters $\sigma_{diff}$ and $\sigma_{dist}$ and the value $I_0$. In the first embodiment, the degree of noise reduction is adjusted based on the pixel values $RAW(x, y)$ and $RAW'(x, y)$ of the endoscopic image before and after the tone transformation process, and the noise reduction process is performed on the pixel value $RAW'(x, y)$.

The process that adjusts the parameter $\sigma_{diff}$ based on the pixel value $RAW(x, y)$ is described in detail below. The parameter $\sigma_{diff}$ is determined based on the pixel value $RAW(x, y)$ of the endoscopic image before the tone transformation process. For example, the parameter $\sigma_{diff}$ is determined using the following expression (13).

$$\sigma_{diff}\{RAW(x,y)\} = \beta \cdot \sqrt{RAW(x,y)} \quad (13)$$

where, β is a predetermined positive value. For example, the value β is determined based on the amount of noise that occurs corresponding to the intensity of light that is incident on the image sensor 232. The parameter $\sigma_{diff}$ is corrected based on the ratio of the pixel values RAW(x, y) and RAW'(x, y) to calculate a parameter $\sigma'_{diff}$ (see the following expression (14)).

$$\sigma'_{diff} = \frac{RAW'(x, y)}{RAW(x, y)} \sigma_{diff} \quad (14)$$

The noise reduction process is performed using the parameter $\sigma'_{diff}$ as the parameter $\sigma_{diff}$ in the expressions (10) to (12).

Noise that occurs due to stochastic fluctuation of the amount of charge generated by photoelectric conversion is referred to as "shot noise". When shot noise is predominant as noise in the captured image, the amount of noise increases by a factor of √2 when the intensity of the incident light is doubled. Therefore, the amount of noise can be appropriately reduced by performing the noise reduction process based on the pixel value RAW(x, y) (see expression (13)). The amount of noise in the endoscopic image that has increased or decreased due to the tone transformation process can be appropriately reduced by correcting the parameter $\sigma_{diff}$ based on the ratio of the pixel values RAW(x, y) and RAW'(x, y) (see expression (14)).

The parameter $\sigma_{dist}$ and the value $I_0$ may be set in the same manner as the parameter $\sigma_{diff}$. The parameter $\sigma_{dist}$ and the value $I_0$ may be arbitrarily determined as long as the degree of noise reduction is controlled corresponding to the pixel value RAW(x, y). The parameter $\sigma_{diff}$ is corrected based on the ratio of the pixel values RAW(x, y) and RAW'(x, y).

2.15. Modified Parameter ($\sigma_{diff}$) Setting Example

In the first embodiment, the upper limit and the lower limit may be set for the parameter $\sigma_{diff}$. A problem in which noise is extremely reduced, or a problem in which noise is not reduced can be eliminated by setting the upper limit and the lower limit for the parameter $\sigma_{diff}$.

Although an example in which the parameter $\sigma_{diff}$ corresponding to the pixel value RAW(x, y) is calculated has been described above, the configuration is not limited thereto. For example, a plurality of parameters $\sigma_{diff}$ may be provided in advance, and may be selectively used based on the pixel value RAW(x, y).

Although an example in which the parameter $\sigma_{diff}$ is determined based on the pixel value RAW(x, y) has been described above, the configuration is not limited thereto. For example, the parameter $\sigma_{diff}$ may be determined based on the pixel value RAW'(x, y).

Although an example in which the parameter $\sigma_{diff}$ is corrected based on the ratio of the pixel values RAW(x, y) and RAW'(x, y) has been described above, the configuration is not limited thereto. For example, the parameter $\sigma_{diff}$ may be corrected based on the difference between the pixel values RAW(x, y) and RAW'(x, y).

Although an example in which the noise reduction process is implemented by the bilateral filtering process has been described above, the configuration is not limited thereto. An arbitrary noise reduction process may be used as long as the degree of noise reduction can be adjusted. When using another noise reduction process, the degree of noise reduction may be adjusted based on the pixel value RAW(x, y) in the same manner as in the case of using the above bilateral filtering process, and the noise reduction process may then be performed.

2.16. Modification of Exposure Control Process

Although an example in which the automatic exposure control section 320 controls the intensity of white light emitted from the white light source 110 has been described above, the configuration is not limited thereto. The automatic exposure control section 320 may have an arbitrary configuration as long as the automatic exposure control section 320 can control the brightness of the endoscopic image.

For example, the imaging section 230 may include an aperture (not illustrated in the drawings), and the automatic exposure control section 320 may control the intensity of light incident on the image sensor 232 by controlling the aperture value of the aperture. In this case, the intensity of light incident in the image sensor 232 can be reduced by increasing the aperture value.

The automatic exposure control section 320 may control the brightness of the endoscopic image by controlling the exposure time of the image sensor 232. In this case, the brightness of the endoscopic image can be reduced by reducing the exposure time.

The image processing section 330 may further have a function of applying a gain to the pixel values of the endoscopic image, and the automatic exposure control section 320 may control the brightness of the endoscopic image by controlling the gain. In this case, the brightness of the endoscopic image can be reduced by decreasing the gain.

According to the first embodiment, an automatic exposure control device includes an image acquisition section, the angle-of-view information acquisition section 310, and the automatic exposure control section 320 (see FIG. 3). The image acquisition section acquires an image that has been captured by an imaging optical system, and includes an image of the object 10, the imaging optical system receiving reflected light, the reflected light being light that has been applied to the object, and reflected by the object 10. The angle-of-view information acquisition section 310 acquires the angle-of-view information that indicates the angle of view of the imaging optical system when the image has been captured. The automatic exposure control section 320 performs the automatic exposure control process that controls automatic exposure based on the acquired angle-of-view information.

For example, the image acquisition section corresponds to the A/D conversion section 233 illustrated in FIG. 3, an interface section (not illustrated in the drawings) that receives image data from the removable insertion section 200, or the like. The imaging optical system corresponds to the objective lens 231 and the image sensor 232 illustrated in FIG. 3, for example.

According to the above configuration, it is possible to implement an appropriate exposure control process regardless of the field-of-view range. Specifically, since the exposure of the captured image can be controlled corresponding to the angle of view of the endoscope, it is possible to implement an appropriate exposure control process that suppresses blown out highlights or blocked up shadows within the main observation target range at an arbitrary angle of view of the endoscope. For example, when screening a hollow tubular organ, the side field of view (i.e., observation range) can be observed in an appropriate exposure state, and a situation in which a lesion is missed can be suppressed, as described above with reference to FIG. 2C. Moreover, since the exposure control process is automatically performed corresponding to the angle of view, the user need not manually switch the exposure setting, and the burden imposed on the user can be reduced.

Note that the term "angle-of-view information" used herein refers to information that indicates the angle of view of the scope, and corresponds to the field-of-view range (viewing angle) captured by the scope. For example, the angle-of-view information may be information that indicates the angle of view, or may be information that indicates the normalized angle of view, or may be information that indicates the encoded angle of view or normalized angle of view. The angle-of-view information may be information that indicates the maximum angle of view of the scope when a zoom operation is not performed (first embodiment), or may be information that indicates the angle of view that has changed along with a zoom operation (second embodiment).

The automatic exposure control section 320 may calculate the automatic exposure evaluation value for evaluating the exposure state within the image based on the angle-of-view information and the pixel values of the image, and perform the automatic exposure control process based on the calculated automatic exposure evaluation value.

Specifically, the automatic exposure control section 320 may include the automatic exposure area setting section 321 (see FIG. 5). As described above with reference to FIG. 6, the automatic exposure area setting section 321 may set the automatic exposure area having the size $W_1$ and $H_1$ corresponding to the angle-of-view information within the image. The automatic exposure control section 320 may calculate the automatic exposure evaluation value based on the pixel values of the pixels within the automatic exposure area.

More specifically, the automatic exposure area setting section 321 may set the automatic exposure area to have a larger size as the angle of view indicated by the angle-of-view information is wider, as described above with reference to FIG. 7 and the expressions (1) and (2).

It is difficult to appropriately control the exposure of the entire image when the angle of view is large, as described above with reference to FIG. 2C and the like. According to the first embodiment, since the exposure control process can be performed on a large automatic exposure area when the angle of view of the scope is wide, it is possible to implement an appropriate exposure control process on the image over a wide range. For example, when a scope that captures the side field of view is attached, the side field of view can be included in the exposure control range.

The automatic exposure control section 320 may include the automatic exposure weight setting section 322 (see FIG. 5). As described above with reference to FIGS. 8 and 9, the automatic exposure weight setting section 322 may set a weight applied to the pixels within the automatic exposure area as the automatic exposure weight, the automatic exposure area being an area for which the automatic exposure evaluation value is calculated. As described above with reference to the expression (6), the automatic exposure control section 320 may calculate the automatic exposure evaluation value based on the pixel values $Y(x, y)$ of the pixels within the automatic exposure area and the automatic exposure weight $W_L(x, y)$.

Specifically, the automatic exposure weight setting section 322 may set the automatic exposure weight corresponding to the angle of view indicated by the angle-of-view information.

More specifically, as described above with reference to FIG. 8, the automatic exposure weight setting section 322 may set the automatic exposure weight applied to the peripheral area situated on the outer side of the center area of the automatic exposure area to be larger than the automatic exposure weight applied to the center area when the angle-of-view information indicates a second angle of view that is wider than a first angle of view.

According to the above configuration, it is possible to relatively increase the weight applied to the peripheral area within the automatic exposure area when calculating the automatic exposure evaluation value when using a wide-angle scope. This makes it possible to implement the exposure control process that relatively attaches weight to the peripheral area of the image when using a wide-angle scope.

The term "first angle of view" used herein refers to a normal angle of view of an endoscopic scope (e.g., default angle of view). The term "normal angle of view" corresponds to the angle of view at which the front field of view is mainly captured. For example, the term "normal angle of view" refers to the angle of view that does not include the field of view in the direction orthogonal to the optical axis (e.g., an angle of view of less than 180° (e.g., 140°).

The center area of the automatic exposure area refers to an area that includes the center of the automatic exposure area. For example, the center area of the automatic exposure area refers to an area within the distance range of 0 to 0.3 in FIG. 8. The peripheral area situated on the outer side of the center area refers to an area that is included in the automatic exposure area, and is situated on the outer side of the center area. The peripheral area may be an area that encloses the center area, or may be one area or a plurality of areas that do not enclose the center area. For example, the peripheral area refers to an area within the distance range of 0.7 to 1.0 in FIG. 8.

As described above with reference to the expression (5), the automatic exposure weight setting section 322 may set the automatic exposure weight $W_L(x, y)$ based on the pixel value $Y(x, y)$ of the pixel within the automatic exposure area.

Specifically, the automatic exposure weight setting section 322 may increase the automatic exposure weight $W_L(x, y)$ as the luminance value $Y(x, y)$ of the pixel within the automatic exposure area increases.

According to the above configuration, since a pixel having a large luminance value is significantly reflected in the automatic exposure evaluation value, it is possible to implement the exposure control process that relatively attaches weight to an area having a large luminance value. This makes it possible to implement the exposure control process that suppresses occurrence of the blown out highlight area.

The automatic exposure control section 320 may calculate the average value or the sum of the pixel values of the pixels within the automatic exposure area as the automatic exposure evaluation value when the angle-of-view information indicates the first angle of view, and bring the calculated automatic exposure evaluation value close to the automatic exposure target value that is the target of the automatic exposure control process.

For example, the automatic exposure evaluation value V may be calculated using the expression (6) wherein $W_L(x, y)=1$ when the angle of view is a normal angle of view.

According to the above configuration, it is possible to implement the exposure control process that sets a different automatic exposure weight to a scope having a normal angle of view and a wide-angle scope. When a small automatic exposure area has been set corresponding to the angle of view, it is considered that a variation in brightness is small in the automatic exposure area. Therefore, the exposure control process can be uniformly performed on the automatic exposure area by utilizing the average value or the sum of the pixel values as the automatic exposure evaluation value.

As illustrated in FIGS. 12 and 13, the automatic exposure control section 320 may include an automatic exposure area division section that divides the automatic exposure area into a plurality of divided automatic exposure areas R(h, w). In this case, the automatic exposure control section 320 may calculate the average value V(h, w) of the pixel values Y(x, y) of the pixels within each divided automatic exposure area among the plurality of divided automatic exposure areas R(h, w), and perform the automatic exposure control process based on the calculated average value V(h, w), as described above with reference to the expression (9).

This makes it possible to perform the exposure control process corresponding to the brightness distribution in the image. For example, the exposure control process can be performed on the high-luminance area by utilizing a divided area of which the average value V(h, w) is equal to or more than a threshold value. Moreover, the exposure control process that eliminates the effects of the high-luminance area can be performed by utilizing a divided area of which the average value V(h, w) is equal to or smaller than a threshold value.

As described above with reference to the expression (8), the automatic exposure control section 320 may set the maximum value among the pixel values of the pixels within the automatic exposure area to be the automatic exposure evaluation value.

According to the above configuration, it is possible to implement a control process that brings the maximum value among the pixel values of the pixels within the automatic exposure area close to the automatic exposure target value. This makes it possible to implement the exposure control process that suppresses occurrence of the saturated area within the automatic exposure area.

The automatic exposure control section 320 may include the specular reflection area detection section 323 (see FIG. 5). The specular reflection area detection section 323 may detect the specular reflection area based on the pixel values of the pixels within the automatic exposure area, the specular reflection area being an area in which the illumination light is specularly reflected by the object. As described above with reference to the expression (6), the automatic exposure control section 320 may calculate the automatic exposure evaluation value V based on the pixel values of the pixels within the automatic exposure area R excluding the specular reflection area M.

As illustrated in FIG. 14, the automatic exposure control section 320 may include the saturated area detection section 326 that detects the saturated area that is an area within the automatic exposure area in which the pixel values of the pixels are saturated. In this case, the automatic exposure control section 320 may perform the automatic exposure control process based on an area of the saturated area other than the specular reflection area.

More specifically, the automatic exposure control section 320 may set the number of pixels included in an area of the saturated area other than the specular reflection area to be the automatic exposure evaluation value, and reduce the exposure when the number of pixels is larger than a threshold value.

According to the above configuration, it is possible to implement the exposure control process based on the number of pixels of the blown out highlight area within the automatic exposure area. Moreover, since the number of pixels of the blown out highlight area is reduced as compared with the threshold value, occurrence of the blown out highlight area can be suppressed. Moreover, the effects of the specular reflection area that is considered to occur independently of the intensity of light can be suppressed by performing the exposure control process based on the number of pixels excluding the number of pixels included in the specular reflection area.

The automatic exposure control section 320 may perform a control process that brings the automatic exposure evaluation value close to the automatic exposure target value that is the target of the automatic exposure control process (e.g., a control process that causes the absolute difference value between the automatic exposure evaluation value and the automatic exposure target value to be less than a threshold value) as the automatic exposure control process.

According to the above configuration, the automatic exposure evaluation value set corresponding to the angle-of-view information can be brought close to the automatic exposure target value, and an appropriate exposure control process corresponding to the angle of view can be implemented.

As described above in connection with the section "2.9. Modified automatic exposure target value setting example", the automatic exposure control section 320 may set the automatic exposure target value corresponding to the angle-of-view information.

More specifically, the automatic exposure control section 320 may set the automatic exposure target value when the angle-of-view information indicates the second angle of view that is wider than the first angle of view to be smaller than the automatic exposure target value when the angle-of-view information indicates the first angle of view.

As described above with reference to FIG. 2C and the like, the difference in brightness within the image obtained using a wide-angle scope is larger than that of an image obtained using a scope having a normal angle of view, and the blown out highlight area tends to easily occur. According to the above configuration, since the exposure control process is performed so that the automatic exposure area is relatively dark when using a wide-angle scope, it is possible to suppress a situation in which blown out highlights occur in the bright area within the image.

The angle-of-view information acquisition section 310 may acquire the angle-of-view information based on identification information (model ID) that specifies the endoscope system that includes the imaging optical system.

Note that the term "identification information" used herein refers to information that specifies the scope. For example, the identification information is information that corresponds to the type, the serial number, the specification, or the like of the scope. The scope may be removable, or may be fixed to the endoscope system. For example, the scope ID stored in the memory 240 included in the scope is used as the identification information, as described with reference to FIG. 3. Alternatively, the user may input the identification information via the external I/F section 500.

The automatic exposure control section 320 may perform the automatic exposure control process by controlling the intensity of light applied to the object. For example, the exposure control section 324 may control the intensity of the illumination light emitted from the white light source 110, as described above with reference to FIG. 5.

As described above in connection with the section "2.16. Modification of exposure control process", the imaging optical system may include an aperture, and the automatic exposure control section may perform the automatic exposure control process by controlling the aperture value (e.g., F-number) of the aperture.

As described above in connection with the section "2.16. Modification of exposure control process", the imaging optical system may include the image sensor 232 that receives reflected light from the object, and the automatic exposure control section 320 may perform the automatic exposure control process by controlling the imaging exposure time of the image sensor 232.

As described above in connection with the section "2.16. Modification of exposure control process", the image processing section 330 may perform a process that applies a gain to the image, and the automatic exposure control section 320 may perform the automatic exposure control process by controlling the gain.

According to the above configuration, it is possible to control the exposure of the captured image. Note that the exposure control process is not limited to those described above. An arbitrary control process that can adjust the exposure of the captured image may be used for the exposure control process.

As illustrated in FIG. 3, the control device 300 includes the automatic exposure control device, and the image processing section 330 that performs image processing on the image acquired by the image acquisition section.

As illustrated in FIG. 15, the image processing section 330 may include the tone transformation section 332 that performs the tone transformation process on the image obtained by the automatic exposure control process based on the pixel values of the image.

As described above in connection with the section "2.13. Tone transformation section", the tone transformation section 332 performs a space-variant tone transformation process that is adaptively performed corresponding to each local area within the image.

According to the above configuration, the luminance of the low-luminance area within the image can be increased, and the luminance of the high-luminance area within the image can be decreased by the tone transformation process. Specifically, a blown out highlight area or a blocked up shadow area that remains after the exposure control process can be adjusted to have brightness that ensures high visibility. This makes it possible to increase the area of the endoscopic image that is appropriate for observation.

The term "space-variant tone transformation process" used herein refers to a tone transformation process that is adaptively performed corresponding to the position of the local area or the pixel values within the local area. For example, the space-variant tone transformation process is a process that sets the characteristics of a tone transformation curve applied to the local area corresponding to the pixel values within the local area.

As illustrated in FIG. 15, the image processing section 330 may include the noise reduction section 333 that performs a process that reduces noise in the image subjected to the tone transformation process.

Specifically, the noise reduction section 333 may adjust the degree of noise reduction based on at least either the pixel values of the pixels within the image that is not subjected to the tone transformation process or the pixel values of the pixels within the image that has been subjected to the tone transformation process.

More specifically, as described above with reference to the expression (14), the noise reduction section 333 may adjust the degree of noise reduction based on a change in the pixel value of each pixel between the image that is not subjected to the tone transformation process, and the image that has been subjected to the tone transformation process. The change in the pixel value may be at least one of the difference and the ratio of the pixel value of each pixel within the image that is not subjected to the tone transformation process, and the pixel value of each pixel within the image that has been subjected to the tone transformation process.

As described above with reference to the expression (13), the noise reduction section 333 may increase the degree of noise reduction as the change in the pixel value increases.

This makes it possible to control the degree of the noise reduction process corresponding to the gain of the adaptive tone transformation process. As a result, it is possible to appropriately reduce noise that changes along with an increase or decrease in the gain.

Note that the degree of noise reduction refers to a degree by which noise in the image is reduced by the noise reduction process. For example, the degree of noise reduction is indicated by the parameter or the frequency characteristics of a smoothing filter. In the bilateral filter described above with reference to the expressions (10) to (12), the parameters $\sigma_{diff}$ and $\sigma_{dist}$ and the value $I_0$ correspond to the degree of noise reduction. The degree of noise reduction increases as these parameters increase.

The image acquisition section may acquire an image that includes at least an image of the object within the front field of view of the imaging optical system, and an image of the object within the side field of view of the imaging optical system. Specifically, as described above with reference to FIG. 1 and the like, the imaging optical system may include an objective lens for observing the object within the front field of view of the imaging optical system, and the object within the side field of view of the imaging optical system. For example, the viewing angle of the objective lens may be larger than 180°.

According to the above configuration, it is possible to acquire an image that includes the side field of view as the image captured by the wide-angle scope. Moreover, it is possible to observe the back side of folds of a large intestine or the like, as described above with reference to FIG. 2D and the like.

Note that the front field of view (front field-of-view range) refers to a field-of-view range that includes the optical axis direction of the objective lens. The side field of view (side field-of-view range) refers to a field-of-view range that includes the direction orthogonal to the optical axis of the objective lens. For example, the front field of view refers to a range of 0 to 45° with respect to the optical axis, and the side field of view refers to a range of 45 to 135° with respect to the optical axis. Alternatively, the front field of view may be an angle of view of 140° (normal field-of-view range), and the side field of view may be a field-of-view range outside the front field of view. When using the objective lens described with reference to FIG. 1, the field-of-view range corresponding to the light beam LC1 introduced through the surface SF1 may be the front field of view, and the field-of-view range corresponding to the light beam LC2 introduced through the surface SF3 may be the side field of view.

3. Second Embodiment

3.1. Endoscope System

Figure 16:
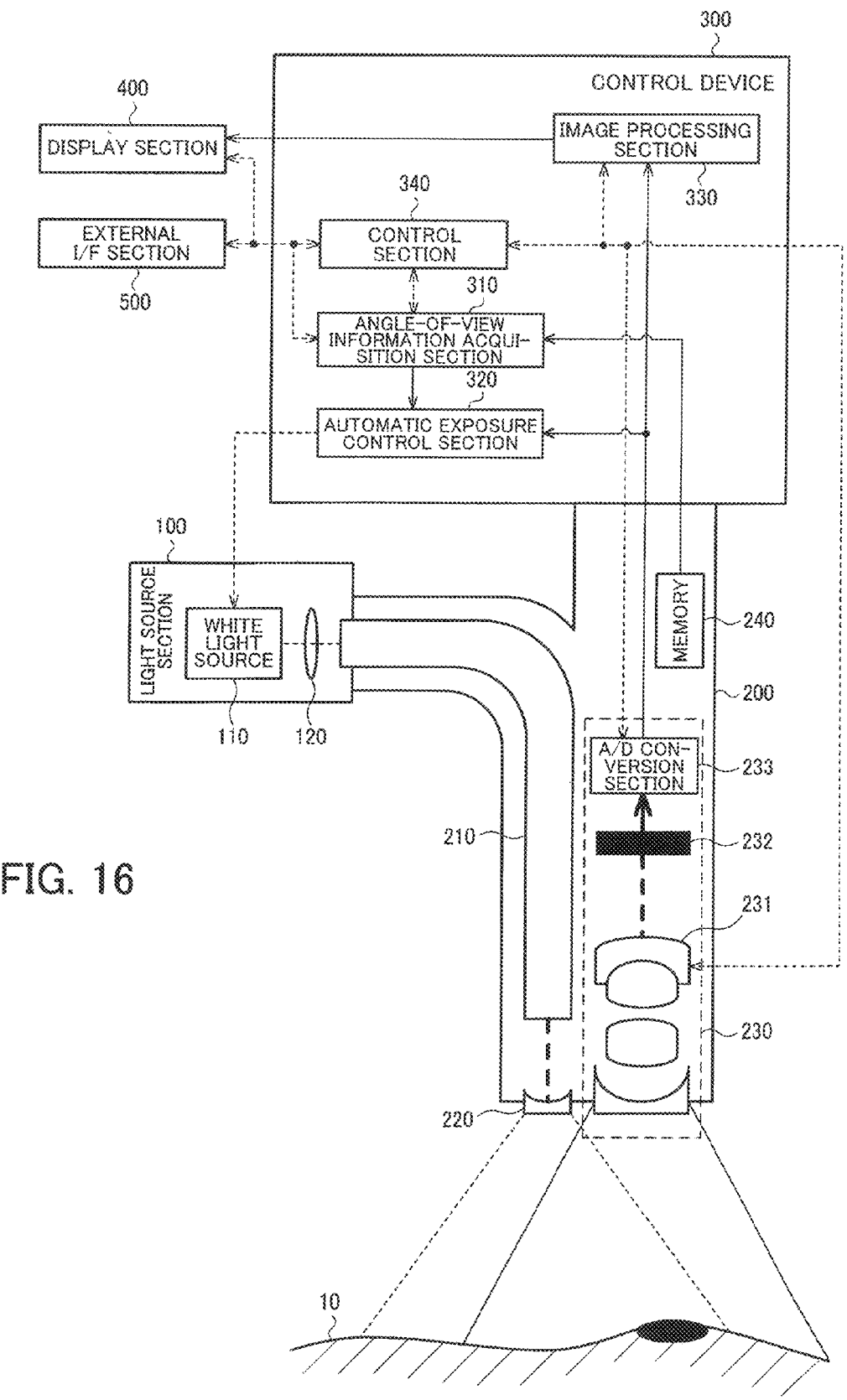
FIG. 16 illustrates a configuration example of an endoscope system according to a second embodiment.

FIG. 16 illustrates a configuration example of an endoscope system according to a second embodiment of the invention. The endoscope system illustrated in FIG. 16 includes a light source section 100, an insertion section 200, a control device 300, a display section 400, and an external I/F section 500. Note that the configuration of each section other than the insertion section 200 and the control device 300 is the same as described above in connection with the first embodiment, and description thereof is appropriately omitted.

The insertion section 200 includes a light guide fiber 210, an illumination lens 220, an imaging section 230, and a memory 240. The elements other than the imaging section 230 are the same as those described above in connection with the first embodiment. The imaging section 230 includes an objective lens 231, an image sensor 232, and an A/D conversion section 233. The elements other than the objective lens 231 are the same as those described above in connection with the first embodiment. The objective lens 230 has a zoom function that can change the magnification of the optical system. The user can change the magnification at an arbitrary timing by operating the external I/F section 500. More specifically, a control section 340 generates a control signal when the user has operated the external I/F section 500, and the magnification of the objective lens 230 is changed based on the control signal.

The control device 300 includes an angle-of-view information acquisition section 310, an automatic exposure control section 320, an image processing section 330, and the control section 340. The elements other than the angle-of-view information acquisition section 310 and the automatic exposure control section 320 are the same as those described above in connection with the first embodiment.

The angle-of-view information acquisition section 310 acquires the magnification of the objective lens 231 based on a control signal generated by the control section 340. The angle-of-view information acquisition section 310 acquires the angle-of-view information based on the magnification and the scope ID stored in the memory 240. Note that the term "angle-of-view information" used in connection with the second embodiment refers to information that corresponds the angle of view that has changed along with a zoom operation, and information that corresponds the angle of view when a zoom operation is not performed. Since the angle of view of the endoscope normally becomes narrow along with a zoom operation, the angle of view when a zoom operation is not performed corresponds to the maximum angle of view described above in connection with the first embodiment. Note that the angle of view that has changed along with a zoom operation is hereinafter referred to as "zoom angle of view". The angle-of-view information acquisition section 310 outputs the acquired angle-of-view information to the automatic exposure control section 320.

The automatic exposure control section 320 includes an automatic exposure area setting section 321, an automatic exposure weight setting section 322, a specular reflection area detection section 323, and an exposure control section 324. Note that the connection configuration of the automatic exposure control section 320 is the same as described above in connection with the first embodiment (e.g., FIG. 5). The process and the effects of each section other than the automatic exposure area setting section 321 and the exposure control section 324 are the same as those described above in connection with the first embodiment. Therefore, description thereof is omitted. The process and the effects of the automatic exposure area setting section 321 and the exposure control section 324 differ from those described above in connection with the first embodiment as to the following points.

The automatic exposure area setting section 321 sets the automatic exposure area within the endoscopic image acquired by the imaging section 230 based on the angle-of-view information acquired by the angle-of-view information acquisition section 310, and outputs information about the automatic exposure area to the exposure control section 324.

Figure 17:
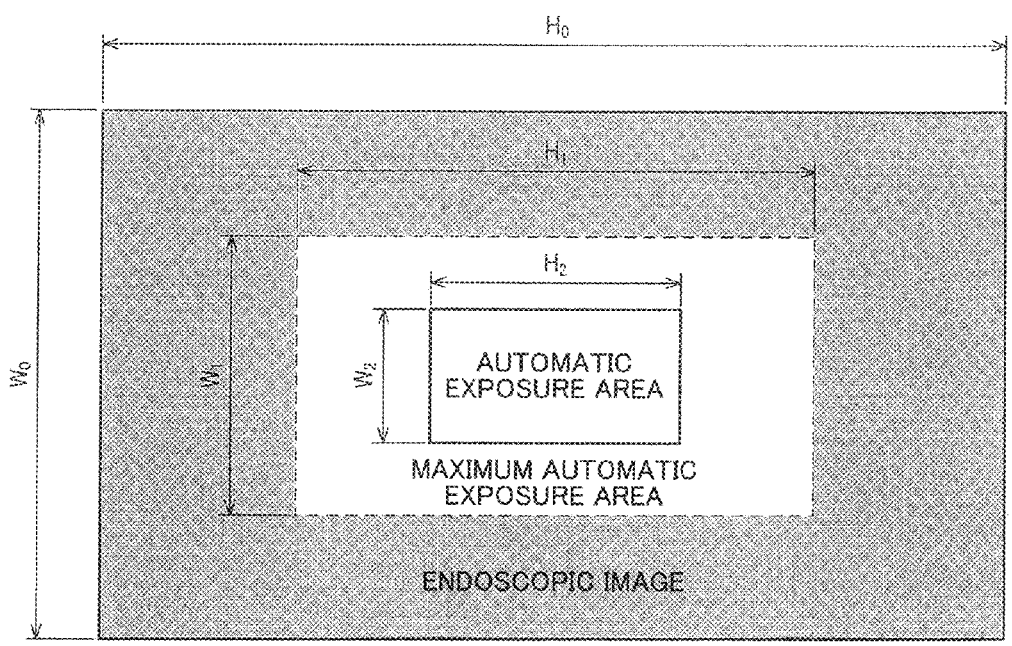
FIG. 17 illustrates a maximum automatic exposure area/automatic exposure area setting example.

As illustrated in FIG. 17, the automatic exposure area setting section 321 sets a maximum automatic exposure area based on the maximum angle of view included in the angle-of-view information, reduces the maximum automatic exposure area based on the zoom angle of view included in the angle-of-view information, and sets the reduced area to be the automatic exposure area. The automatic exposure area setting section 321 sets the maximum automatic exposure area based on the maximum angle of view using the expressions (1) and (2) in the same manner as the automatic exposure area described above in connection with the first embodiment. The relationship between the size ($W_2$ and $H_2$) of the automatic exposure area and the size ($W_1$ and $H_1$) of the maximum automatic exposure area is shown by the following expressions (15) and (16).

$$W_2 = \alpha_1 W_1 \qquad (15)$$

$$H_2 = \alpha_1 H_1 \qquad (16)$$

Figure 18:
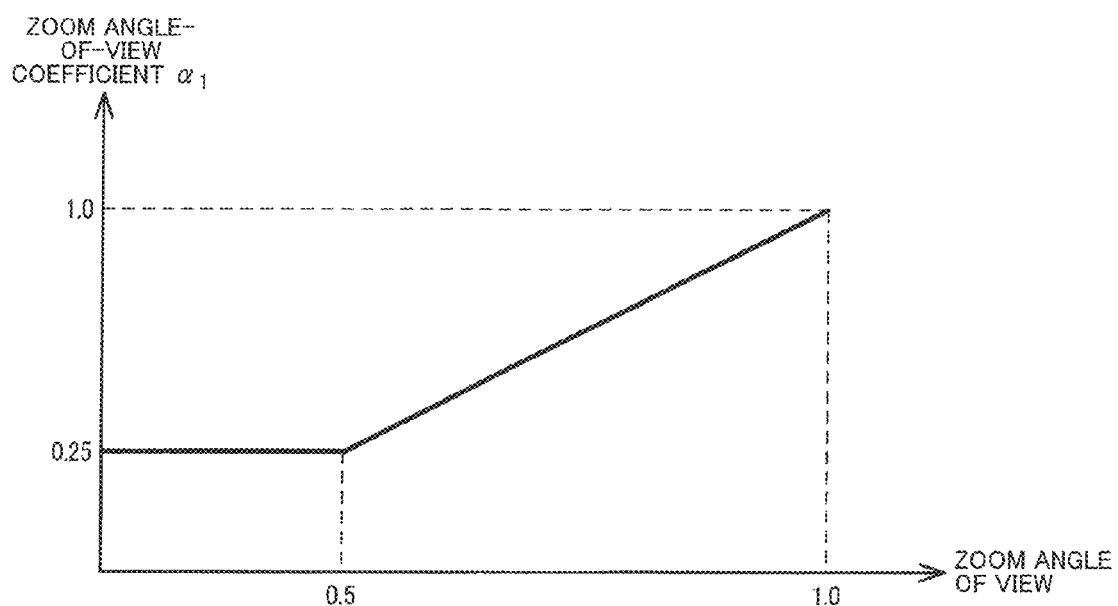
FIG. 18 illustrates a zoom angle-of-view coefficient setting example.

Note that $\alpha_1$ is a zoom angle-of-view coefficient of less than 1.0 that is determined based on the zoom angle of view. FIG. 18 illustrates a zoom angle-of-view coefficient ($\alpha_1$) setting example. In FIG. 18, the zoom angle of view is normalized using the maximum angle of view.

Since the depth of field of the endoscope optical system decreases along with a zoom operation, the in-focus area within the object image also decreases. The automatic exposure area can be reduced as the magnification increases (i.e., as the zoom angle of view decreases) by setting the zoom angle-of-view coefficient $\alpha_1$ as illustrated in FIG. 18. This makes it possible to perform the dimming process only on the in-focus area, and more accurately control the intensity of light applied to the zoom observation target object. Specifically, the dimming process can be implemented so that the zoom observation target object has an appropriate brightness by changing the size of the automatic exposure area corresponding to a change in angle of view along with the zoom operation.

The exposure control section 324 calculates the automatic exposure evaluation value based on the pixel values of the endoscopic image acquired by the imaging section 230, the automatic exposure weight set by the automatic exposure weight setting section 322, and the specular reflection area detected by the specular reflection area detection section 323, and performs the dimming process based on the automatic exposure evaluation value and a given automatic exposure target value. The second embodiment differs from the first embodiment as to the automatic exposure target value setting method.

Specifically, when observing a wide field of view using a wide-field endoscope having a zoom function without performing a zoom operation, the automatic exposure target value is set to be smaller than that during zoom observation. As described above with reference to FIG. 2C, the distance between the wide-field endoscope and the object may differ to a large extent in the front field of view and the side field of view. Therefore, blown out highlights may occur in the front field of view or the side field of view if the automatic exposure target value is not changed corresponding to the magnification. In order to reduce the occurrence frequency of blown out highlights, the automatic exposure target value is set to a small value when observing a wide field of view.

On the other hand, since the field of view becomes narrow during zoom observation as compared with normal observation, the distance between the end of the scope and the object within the field of view does not change to a large extent. Therefore, the intensity of light applied to the object is increased while suppressing blown out highlights by setting the automatic exposure target value to a large value as compared with the case of observing a wide field of view.

3.2. Modification

Although an example in which the maximum automatic exposure area is set based on the maximum angle of view of the scope has been described above, the configuration is not limited thereto. For example, the maximum automatic exposure area having a fixed size may be set independently, of the maximum angle of view. Specifically, the automatic exposure area may be set depending on only the zoom angle of view of the scope.

In this case, the angle-of-view information acquisition section 310 does not receive the scope ID from the memory 240, and receives only the magnification acquired based on the control signal output from the control section 340 as the angle-of-view information. The angle-of-view information acquisition section 310 acquires the zoom angle of view that implements the magnification based on a table stored in advance. According to the above configuration, since it is unnecessary to set the maximum automatic exposure area, the amount of calculations can be reduced.

According to the second embodiment, the imaging optical system (e.g., objective lens 231 and image sensor 232) may be an optical system that can be changed in magnification, as described above with reference to FIG. 16. The angle-of-view information acquisition section 310 may acquire the angle-of-view information based on the magnification of the imaging optical system.

More specifically, the automatic exposure control section 320 may include the automatic exposure area setting section 321. As described above with reference to FIGS. 17 and 18, the automatic exposure area setting section may set the automatic exposure area within the image based on the angle-of-view information so that the automatic exposure area has a smaller size as the magnification increases (i.e., as the angle of view that changes corresponding to the magnification decreases). The automatic exposure control section 320 may calculate the automatic exposure evaluation value based on the pixel values of the pixels within the automatic exposure area, and perform the automatic exposure control process based on the calculated automatic exposure evaluation value.

As described above, the depth of field of the endoscope optical system decreases along with a zoom operation, and the in-focus area within the endoscopic image also decreases. According to the second embodiment, the exposure control target area can be set corresponding to the angle of view of the endoscope that changes along with a zoom operation, and the intensity of light applied to the object within the exposure control target area can be controlled. This makes it possible to more accurately apply light to the in-focus range within the endoscopic image observed at an arbitrary magnification at an intensity appropriate for observation.

The embodiments according to the invention and the modifications thereof have been described above. Note that the invention is not limited to the above embodiments and the modifications thereof. Various modifications and variations may be made of the above embodiments and the modifications thereof without departing from the scope of the invention. A plurality of elements described in connection with the above embodiments and the modifications thereof may be appropriately combined to implement various configurations. For example, some elements may be omitted from the elements described in connection with the above embodiments and the modifications thereof. Some of the elements described in connection with different embodiments or modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

What is claimed is:

1. An automatic exposure control device comprising:
an image acquisition section that acquires an image that has been captured by an imaging optical system that receives reflected light, and includes an image of an object, the reflected light being light that has been applied to the object, and reflected by the object;
an angle-of-view information acquisition section that acquires angle-of-view information that indicates an angle of view of the imaging optical system when the image has been captured; and
an automatic exposure control section that performs an automatic exposure control process that controls automatic exposure based on the acquired angle-of-view information,
the automatic exposure control section including an automatic exposure area setting section that sets an automatic exposure area having a size corresponding to the angle-of-view information within the image,
the automatic exposure control section calculating an automatic exposure evaluation value for evaluating an exposure state within the image based on pixel values of pixels within the automatic exposure area, and performing the automatic exposure control process based on the calculated automatic exposure evaluation value,
the automatic exposure control section including an automatic exposure weight setting section that sets a weight applied to pixels within an automatic exposure area as an automatic exposure weight, the automatic exposure area being an area for which the automatic exposure evaluation value is calculated, and
the automatic exposure control section calculating the automatic exposure evaluation value based on the pixel values of the pixels within the automatic exposure area and the automatic exposure weight.

2. The automatic exposure control device as defined in claim 1,
the automatic exposure area setting section setting the automatic exposure area to have a larger size as the angle of view indicated by the angle-of-view information is wider.

3. The automatic exposure control device as defined in claim 1,
the automatic exposure weight setting section setting the automatic exposure weight corresponding to the angle of view indicated by the angle-of-view information.

4. The automatic exposure control device as defined in claim 3,
the automatic exposure weight setting section setting the automatic exposure weight applied to a peripheral area situated on an outer side of a center area of the automatic exposure area to be larger than the automatic exposure weight applied to the center area when the angle-of-view information indicates a second angle of view that is wider than a first angle of view.

5. The automatic exposure control device as defined in claim 1,
the automatic exposure weight setting section setting the automatic exposure weight based on the pixel values of the pixels within the automatic exposure area.

6. The automatic exposure control device as defined in claim 5,
the automatic exposure weight setting section increasing the automatic exposure weight as luminance values of the pixels within the automatic exposure area increase.

7. The automatic exposure control device as defined in claim 1,
the automatic exposure control section calculating an average value or sum of the pixel values of the pixels within the automatic exposure area as the automatic exposure evaluation value when the angle-of-view information indicates a first angle of view, and bringing the calculated automatic exposure evaluation value close to an automatic exposure target value that is a target of the automatic exposure control process.

8. The automatic exposure control device as defined in claim 1,
the automatic exposure control section including an automatic exposure area division section that divides the automatic exposure area into a plurality of divided automatic exposure areas, and
the automatic exposure control section calculating an average value of the pixel values of the pixels within each divided automatic exposure area among the plurality of divided automatic exposure areas, and performing the automatic exposure control process based on the calculated average value.

9. The automatic exposure control device as defined in claim 1,
the automatic exposure control section setting a maximum value among the pixel values of the pixels within the automatic exposure area to be the automatic exposure evaluation value.

10. The automatic exposure control device as defined in claim 1,
the automatic exposure area setting section including a specular reflection area detection section that detects a specular reflection area based on the pixel values of the pixels within the automatic exposure area, the specular reflection area being an area in which illumination light is specularly reflected by the object, and
the automatic exposure control section calculating the automatic exposure evaluation value based on the pixel values of the pixels within the automatic exposure area excluding the specular reflection area.

11. The automatic exposure control device as defined in claim 10,
the automatic exposure area setting section including a saturated area detection section that detects a saturated area that is an area within the automatic exposure area in which the pixel values of the pixels are saturated, and
the automatic exposure control section performing the automatic exposure control process based on an area of the saturated area other than the specular reflection area.

12. The automatic exposure control device as defined in claim 11,
the automatic exposure control section setting a number of pixels included in the area of the saturated area other than the specular reflection area to be the automatic exposure evaluation value, and reducing an exposure when the number of pixels is larger than a threshold value.

13. The automatic exposure control device as defined in claim 1,
the automatic exposure control section performing a control process that brings the automatic exposure evaluation value close to an automatic exposure target value as the automatic exposure control process, the automatic exposure target value being a target of the automatic exposure control process.

14. The automatic exposure control device as defined in claim 13,
the automatic exposure control section setting the automatic exposure target value corresponding to the angle-of-view information.

15. The automatic exposure control device as defined in claim 14,
the automatic exposure control section setting the automatic exposure target value when the angle-of-view information indicates a second angle of view that is wider than a first angle of view to be smaller than the automatic exposure target value when the angle-of-view information indicates the first angle of view.

16. The automatic exposure control device as defined in claim 1,
the angle-of-view information acquisition section acquiring the angle-of-view information based on identification information that specifies an endoscope system that includes the imaging optical system.

17. The automatic exposure control device as defined in claim 1,
the imaging optical system being an optical system that can be changed in magnification, and
the angle-of-view information acquisition section acquiring the angle-of-view information based on the magnification of the imaging optical system.

18. The automatic exposure control device as defined in claim 17,
the automatic exposure control section including an automatic exposure area setting section that sets an automatic exposure area within the image based on the angle-of-view information so that the automatic exposure area has a smaller size as the magnification increases, and
the automatic exposure control section calculating the automatic exposure evaluation value based on pixel values of pixels within the automatic exposure area, and performing the automatic exposure control process based on the calculated automatic exposure evaluation value.

19. The automatic exposure control device as defined in claim 1,
the automatic exposure control section performing the automatic exposure control process by controlling an intensity of the light applied to the object.

20. The automatic exposure control device as defined in claim 1,
the imaging optical system including an aperture, and
the automatic exposure control section performing the automatic exposure control process by controlling an aperture value of the aperture.

21. The automatic exposure control device as defined in claim 1,
the imaging optical system including an image sensor that receives the reflected light, and
the automatic exposure control section performing the automatic exposure control process by controlling an imaging exposure time of the image sensor.

22. The automatic exposure control device as defined in claim 1,
the image acquisition section acquiring the image that includes at least an image of the object within a front field of view of the imaging optical system, and an image of the object within a side field of view of the imaging optical system.

23. The automatic exposure control device as defined in claim 22,
the imaging optical system including an objective lens for observing the object within the front field of view of the imaging optical system, and the object within the side field of view of the imaging optical system.

24. The automatic exposure control device as defined in claim 23,
a viewing angle of the objective lens being larger than 180°.

25. A control device comprising:
the automatic exposure control device as defined in claim 1; and
an image processing section that performs image processing on the image acquired by the image acquisition section.

26. The control device as defined in claim 25,
the image processing section including a tone transformation section that performs a tone transformation process on the image obtained by the automatic exposure control process.

27. The control device as defined in claim 26,
the tone transformation section performing a space-variant tone transformation process that is adaptively performed corresponding to each local area within the image.

28. The control device as defined in claim 26,
the image processing section including a noise reduction section that performs a process that reduces noise in the image subjected to the tone transformation process.

29. The control device as defined in claim 28,
the noise reduction section adjusting a degree of noise reduction based on at least either pixel values of pixels within the image that is not subjected to the tone transformation process or the pixel values of the pixels within the image that has been subjected to the tone transformation process.

30. The control device as defined in claim 28,
the noise reduction section adjusting a degree of noise reduction based on a change in pixel value of each pixel between the image that is not subjected to the tone transformation process and the image that has been subjected to the tone transformation process, and
the change in the pixel value being at least one of a difference and a ratio of the pixel value of each pixel within the image that is not subjected to the tone transformation process and the pixel value of each pixel within the image that has been subjected to the tone transformation process.

31. The control device as defined in claim 30,
the noise reduction section increasing the degree of noise reduction as the change in the pixel value increases.

32. The control device as defined in claim 25,
the image processing section performing a process that applies a gain to the image, and
the automatic exposure control section performing the automatic exposure control process by controlling the gain.

33. An endoscope system comprising:
a light source section that emits light that is applied to an object;
an imaging section that captures an image including an image of the object using an imaging optical system that receives reflected light, the reflected light being the light that has been applied to the object, and reflected by the object;
an angle-of-view information acquisition section that acquires angle-of-view information that indicates an angle of view of the imaging optical system when the image has been captured; and
an automatic exposure control section that performs an automatic exposure control process that controls that controls automatic exposure based on the acquired angle-of-view information,
the automatic exposure control section including an automatic exposure area setting section that sets an automatic exposure area having a size corresponding to the angle-of-view information within the image,
the automatic exposure control section calculating an automatic exposure evaluation value for evaluating an exposure state within the image based on pixel values of pixels within the automatic exposure area, and performing the automatic exposure control process based on the calculated automatic exposure evaluation value,
the automatic exposure control section including an automatic exposure weight setting section that sets a weight applied to pixels within an automatic exposure area as an automatic exposure weight, the automatic exposure area being an area for which the automatic exposure evaluation value is calculated, and
the automatic exposure control section calculating the automatic exposure evaluation value based on the pixel values of the pixels within the automatic exposure area and the automatic exposure weight.

34. An automatic exposure control method comprising:
acquiring an image that has been captured by an imaging optical system that receives reflected light, and includes an image of an object, the reflected light being light that has been applied to the object, and reflected by the object;
acquiring angle-of-view information that indicates an angle of view of the imaging optical system when the image has been captured;
setting an automatic exposure area having a size corresponding to the angle-of-view information within the image;
calculating an automatic exposure evaluation value for evaluating an exposure state within the image based on pixel values of pixels within the automatic exposure area; and performing an automatic exposure control process that controls automatic exposure based on the calculated automatic exposure evaluation value, wherein the setting comprises setting a weight applied to pixels within an automatic exposure area as an automatic exposure weight, the automatic exposure area being an area for which the automatic exposure evaluation value is calculated, and wherein the calculating calculates the automatic exposure evaluation value based on the pixel values of the pixels within the automatic exposure area and the automatic exposure weight.

* * * * *